US011020422B2

(12) United States Patent
McKew et al.

(10) Patent No.: US 11,020,422 B2
(45) Date of Patent: *Jun. 1, 2021

(54) CYCLODEXTRIN FOR THE TREATMENT OF LYSOSOMAL STORAGE DISEASES

(71) Applicant: The United States of America, as represented by the Secretary, Dept. of Health and Human Services, Rockville, MD (US)

(72) Inventors: John McKew, Poolesville, MD (US); Wei Zheng, Potomac, MD (US); Miao Xu, Hangzhou (CN); Manju Swaroop, Gaithersburg, MD (US); Juan J. Marugan, Gaithersburg, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/620,753

(22) Filed: Jun. 12, 2017

(65) Prior Publication Data
US 2018/0110798 A1   Apr. 26, 2018

Related U.S. Application Data

(63) Continuation of application No. 14/419,471, filed as application No. PCT/US2013/053527 on Aug. 3, 2013, now abandoned.

(60) Provisional application No. 61/679,668, filed on Aug. 3, 2012.

(51) Int. Cl.
*A61K 31/724* (2006.01)
*A61K 31/335* (2006.01)
*A61K 45/06* (2006.01)
*C08B 37/16* (2006.01)
*G01N 33/92* (2006.01)
*A61K 31/355* (2006.01)

(52) U.S. Cl.
CPC .......... *A61K 31/724* (2013.01); *A61K 31/355* (2013.01); *A61K 45/06* (2013.01); *C08B 37/0012* (2013.01); *G01N 33/92* (2013.01)

(58) Field of Classification Search
CPC .... A61K 45/06; A61K 31/355; A61K 31/724; A61K 2300/00; C08B 37/0012; G01N 33/92
USPC .......................................... 514/58
See application file for complete search history.

(56) References Cited

U.S. PATENT DOCUMENTS

| | | | |
|---|---|---|---|
| 4,727,064 A | 2/1988 | Pitha | |
| 5,262,404 A | 11/1993 | Weisz et al. | |
| 5,376,645 A | 12/1994 | Stella et al. | |
| 6,407,079 B1 | 6/2002 | Müller et al. | |
| 6,528,642 B1 | 3/2003 | Duval et al. | |
| 9,044,451 B2 | 6/2015 | Zheng et al. | |
| 2001/0056080 A1 | 12/2001 | Woo et al. | |
| 2004/0076591 A1 | 4/2004 | Nelson et al. | |
| 2006/0025380 A1 | 2/2006 | Thorsteinsson | |
| 2009/0258001 A1* | 10/2009 | Ponath | C07K 16/2809 424/130.1 |
| 2011/0028432 A1 | 2/2011 | Cataldo et al. | |
| 2015/0216895 A1 | 8/2015 | McKew et al. | |

FOREIGN PATENT DOCUMENTS

| | | | |
|---|---|---|---|
| JP | 2007-504166 A | 3/2007 | |
| WO | WO2010/138802 A2 * | 12/2010 | ........... A61K 31/715 |
| WO | WO-2010/138802 A2 | 12/2010 | |
| WO | WO2012/012473 A1 * | 1/2012 | ........... A61K 31/355 |
| WO | WO-2012/012473 A1 | 1/2012 | |
| WO | WO-2014/022841 A1 | 2/2014 | |
| WO | WO-2015/087016 A1 | 6/2015 | |

OTHER PUBLICATIONS

The Merck Manual, 1992, pp. 1049-1051.*
Szejtli. Medicinal Research Reviews, 1994, 14(3), 353-386.*
Aqul et al, The Journal of Neuroscience, Jun. 22, 2011, 31(25), 9404-9413.*
Peake et al, FEBS Letters, 2010, 584, 2731-2739.*
Stern, Warren C., Drug News and Perspectives, Feb. 1989, 410-415.*
Australian First Examination Report, Australian Application No. 2013296170, dated May 5, 2017, 4 pages.
PCT International Search Report and Written Opinion, International Application No. PCT/US2013/053527, dated Oct. 16, 2013, 14 Pages.
PCT International Preliminary Report on Patentability, International Application No. PCT/US2013/053527, dated Feb. 3, 2015, 10 Pages.
PCT International Search Report and Written Opinion, International Application No. PCT/US2016/036753, dated Aug. 30, 2016, 13 Pages.
State Intellectual Property Office, Chinese Patent Application No. 201380052023.0, dated Jul. 28, 2016, 17 Pages.
United States Office Action, U.S. Appl. No. 14/419,471, dated Apr. 19, 2016, 18 Pages.
United States Office Action, U.S. Appl. No. 14/419,471, dated Dec. 12, 2016, 16 Pages.
Abi-Mosleh, L., et al., "Cyclodextrin overcomes deficient lysosome-to-endoplasmic reticulum transport of cholesterol in Niemann-Pick type C cells," Proceedings of the National Academy of Sciences, 2009, pp. 19316-19321, vol. 106, No. 46.
Alvarez, A.R., et al., "Imatinib therapy blocks cerebellar apoptosis and improves neurological symptoms in a mouse model of Niemann-Pick type C disease," FASEB Journal, 2008, pp. 3617-3627, vol. 22.
Aqul, A., et al., "Unesterified Cholesterol Accumulation in Late Endosomes/Lysosomes Causes Neurodegeneration and Is Prevented by Driving Cholesterol Export from This Compartment," J Neurosci. 2011, pp. 9404-9413, vol. 31, No. 25.
Beers, M. H., et al., The Merck Manual of Diagnosis and Therapy, 1992, pp. 1049-1051, Merck & Co., Inc., Rahway, N.J.
Brewster, M. E., et al., "An intravenous toxicity study of 2-hydroxypropyl-B-cyclodextrin, a useful drug solubilizer, in rats and monkeys," International Journal of Pharmaceutics, 1990, pp. 231-243, vol. 59.

(Continued)

Primary Examiner — Ganapathy Krishnan

(57) ABSTRACT

The invention provides for methods of treating lysosomal storage disorders and/or reduction of non-cholesterol lipids, using cyclodextrin compounds, including in combination with other therapeutics, including vitamin E.

6 Claims, 26 Drawing Sheets

(56) References Cited

OTHER PUBLICATIONS

Byun, K., et al., "Alteration of the glutamate and GABA transporters in the hippocampus of the Niemann-Pick disease, type C mouse using proteomic analysis," Proteomics, 2006, pp. 1230-1236, No. 6.
Camargo, F., et al., "Cyclodextrins in the treatment of a mouse model of Niemann-Pick C disease," Life Sciences, 2001, pp. 131-142, vol. 70, No. 2.
Cantz, M., et al., "Disorders of Glycoprotein Degradation," J. Inherit. Metab. Dis., 1990, pp. 523-537, vol. 13.
Carstea, E.D., et al., "Niemann-Pick C1 Disease Gene: Homology to mediators of cholesterol homeostasis," Science, 1997, pp. 228-231, vol. 277.
Chen, F., et al., "Cyclodextrin Induces Calcium-Dependent Lysosomal Exocytosis." PLoS One, 2010, vol. 5, No. 11, e15054, 7 Pages.
Chien, Y.H., et al., "Long-term efficacy of miglustat in paediatric patients with Niemann-Pick disease type C," Journal of Inherited Metabolic Disease, 2013, pp. 129-137, vol. 36.
Choi, H. Y., et al., "Impaired ABCA1-dependent lipid efflux and hypoalphalipoproteinemia in human Niemann-Pick type C disease." J Biol Chem, 2003, pp. 32569-32577, vol. 278, No. 35.
Cluzeau, C.V.M., et al., "Microarray expression analysis and identification of serum biomarkers for Niemann-Pick disease, type C1," Human Molecular Genetics, 2012, pp. 3632-3646, vol. 21, No. 16.
Cologna, S.M., et al., "Quantitative proteomic analysis of Niemann-Pick disease, type C1 cerebellum identifies protein biomarkers and provides pathological insight," PloS One, 2012, vol. 7, No. 10, e47845.
Crumling, M. A., et al. , "Hearing loss and hair cell death in mice given the cholesterol-chelating agent hydroxypropyl-β-cyclodextrin." PLoS One, 2012, vol. 7. No. 12, e53280.
Cruz-Pardos, S., et al., "Treatment with cyclodextrin for Niemann Pick's disease," Farm Hospital, 2013, pp. 263-272, vol. 37, No. 3. (with machine translation of first page).
Davidson, C. D., et al., "Chronic Cyclodextrin Treatment of Murine Niemann-Pick C Disease Ameliorates Neuronal Cholesterol and Glycosphingolipid Storage and Disease Progression," PLoS One, 2009, vol. 4, No. 9, 15 Pages.
Davidson, C., et al., Poster: "Combinatorial therapy for Niemann-Pick type C disease: treatment of an NPC1 murine model with 2-hydroxypropyl-beta-cyclodextrin and miglustat," WORLDSymposium, 2015.
Davidson, C. D., et al., "Efficacy of Different Cyclodextrins in the Treatment of Niemann-Pick type C Disease," Jun. 2012, Abstract, [online] [Retrieved on Jul. 20, 2016] Retrieved from the Internet <URL:http://niemannpick.nd.edu/assets/69394/abstracts_in_speaking_order.pdf>.
Davidson, C., et al., "Different cyclodextrins for the treatment of Niemann-Pick disease type C," Molecular Genetics and Metabolism, 2016, S14-S124, vol. 117 (Abstract).
Davidson, C., et al., "Chronic cyclodextrin administration ameliorates clinical symptoms and storage accumulation in Niemann-Pick Type C1 mice," Molecular Genetics and Metabolism, 2009, S12-S47, vol. 96 (Abstract).
Davidson, C.D., et al., "Efficacy and ototoxicity of different cyclodextrins in Niemann-Pick C disease," Annals of Clinical and Translational Neurology, 2016, pp. 366-380, vol. 3., No. 5.
Decroocq, C., et al., "Cyclodextrin-Based Iminosugar Click Clusters: The First Examples of Multivalent Pharmacological Chaperones for the Treatment of Lysosomal Storage Disorders," ChemBioChem, 2012, pp. 661-664, vol. 13, No. 5.
De Windt, A., et al., "Gene set enrichment analyses revealed several affected pathways in Niemann-pick disease type C fibroblasts," DNA and Cell Biology, 2007, pp. 665-671, vol. 26, No. 9.
Elrick, M.J., et al, "Autophagic dysfunction in a lysosomal storage disorder due to impaired proteolysis," Autophagy, 2013, pp. 234-235, vol. 9, No. 2.
European Medicines Agency, Committee for Human Medicinal Products, EMA/CHMP/333892/2013, Nov. 20, 2014: "Background review for cyclodextrins used as excipients." [online][Retrieved on Feb. 3, 2017] Retrieved from the Internet <URL: http://www.ema.europa.eu/docs/en_GB/document_library/Report/2014/12/WC500177936.pdf>.
European Medicines Agency, Committee for Human Medicinal Products, EMA/CHMP/334655/2013, Nov. 20, 2014: "Background review for the excipient propylene glycol." [online][Retrieved on Feb. 3, 2017] Retrieved from the Internet <URL: http://www.ema.europa.eu/docs/en_GB/document_library/Report/2014/12/WC500177936.pdf>.
Fenyvesi, F., et al., "Fluorescently labeled methyl-beta-cyclodextrin enters intestinal epithelial Caco-2 cells by fluid-phase endocytosis," PLoS One 2014, 9, No. 1., e84856.
Garcia-Robels, A. A., et al., "Use of 2 hydroxypropyl-beta-cyclodextrin therapy in two adult Niemann Pick Type C patients," Journal of the Neurological Sciences, 2016, pp. 65-67, vol. 366.
Gelsthorpe, M.E., et al., "Niemann-Pick type C1 I1061T mutant encodes a functional protein that is selected for endoplasmic reticulum-associated degradation due to protein misfolding," The Journal of Biological Chemistry, 2008, pp. 8229-8236, vol. 283, No. 13.
Ginocchio, V.M., et al., "Efficacy of miglustat in Niemann-Pick C disease: a single centre experience. Molecular genetics and metabolism," 2013, pp. 329-335, vol. 110, No. 3.
Gould, S., et al., "2-Hydroxypropyl-b-cyclodextrin (HP-b-CD): A toxicology review," Food and Chemical Toxicology, 2005, pp. 1451-1459, vol. 43.
Heron, B., et al., "Miglustat therapy in the French cohort of paediatric patients with Niemann-Pick disease type C," Orphanet Journal of Rare Diseases, 2012, vol. 7, No. 36, 14 Pages.
Hastings, C. A., et al., "Clinical Experience with Intravenous and Intrathecal Infusions of Hydroxy-Propyl-Beta-Cyclodextrin in Identical Twin Patients with Niemann-Pick Type C Disease," Jun. 2011, Abstract, [online][Retrieved on Jul. 20, 2016] Retrieved from the Internet <URL:http://niemannpick.nd.edu/assets/52702/all_abstracts.pdf>.
Hempel, C., "FDA Filing Requesting to put Cyclodextrin into the Brains of the Addi and Cassi—Aug. 2010," [online][Retrieved on Sep. 16, 2016] Retrieved from the Internet <URL:http://addiandcassi.com/wordpress/wp-content/uploads/Hempel-Cyclodextrin-Intrathecal-FDA-Filing-2010-Aug.pdf>.
Hempel, C., "FDA Investigational New Drug Application Documents for Cyclodextrin Treatment for Niemann Pick Type C Disease" Sep. 13, 2009, [online] Retrieved from the Internet <URL:http://addiandcassi.com/fda-investigational-new-drug-application-documents-for-cyclodextrin-treatment-for-niemann-pick-type-c-disease/>.
Hempel, C., "Dr. Caroline Hastings Submission Letter to FDA: Investigational New Drug Application—May 2009," [online][Retrieved on Sep. 16, 2016] Retrieved from the Internet <URL:http://addiandcassi.com/wordpress/wp-content/uploads/2009/09/FDA-Caroline-Hastings-Submission-Letter-May-2009.pdf>.
Hempel, C., "Dear British Media—Feel Free to Call or Email!," Mar. 26, 2009, [online] [Retrieved on Jan. 20, 2016] Retrieved from the Internet <URL:http://addiandcassi.com/dear-british-media/>.
Irie, T., et al., "Pharmaceutical Applications of Cyclodextrins. III. Toxicological Issues and Safety Evaluation," Journal of Pharmaceutical Sciences, 1997, pp. 147-162, vol. 86, No. 2.
Jiang, H., et al., "Development and validation of sensitive LC-MS/MS assays for quantification of HP-β-CD in human plasma and CSF," Journal of Lipid Research, 2014, pp. 1537-1548, vol. 55, No. 7.
Jiang, X., et al., "Development of a bile acid-based newborn screen for Niemann-Pick disease type C," Science Translational Medicine, 2016, vol. 8, Issue 337, 11 Pages.
King, K., et al., "Auditory Phenotype of Niemann-Pick Disease, Type C1," Ear Hear, 2014, pp. 110-117, vol. 35, No. 1.
Ko, D.C., et al., "Cell-autonomous death of cerebellar purkinje neurons with autophagy in Niemann-Pick type C disease," PLoS Genetics, 2005, pp. 81-95, vol. 1, No. 1.
Kondo, Y., et al., "In vitro evaluation of 2-hydroxyalkylated beta-cyclodextrins as potential therapeutic agents for Niemann-Pick Type C disease," Molecular Genetics and Metabolism, 2016, pp. 214-219, vol. 118.

(56) References Cited

OTHER PUBLICATIONS

Lachmann, R.H., "Treatment with miglustat reverses the lipid-trafficking defect in Niemann-Pick disease type C," Neurobiology of Disease, 2004, pp. 654-658, vol. 16, No. 3.
Leigh-Paffenroth, E., "Objective measures of ototoxicity," SIG 6 Perspectives on Hearing and Hearing Disorders: Research and Diagnostics, 2005, pp. 10-16, vol. 9, No. 1.
Liao, G., et al., "Allopregnanolone treatment delays cholesterol accumulation and reduces autophagic/lysosomal dysfunction and inflammation in Npc1-/- mouse brain," Brain Research, 2009, pp. 140-151, 1270.
Lieberman, A.P., et al., "Autophagy in lysosomal storage disorders," Autophagy, 2012, pp. 719-730, vol. 8, No. 5.
Liu, B., et al., "Genetic variations and treatments that affect the lifespan of the NPC1 mouse," Journal of Lipid Research, 2008, pp. 663-669, vol. 49.
Liu, B., et al., "Reversal of defective lysosomal transport in NPC disease ameliorates liver dysfunction and neurodegeneration in the npc1-/- mouse," Proceedings of the National Academy of Sciences, 2009, pp. 2377-2382, vol. 106, No. 7.
Liu, B., et al., "Cyclodextrin overcomes the transport defect in nearly every organ of NPC1 mice leading to excretion of sequestered cholesterol as bile acid," Journal of Lipid Research, 2010, pp. 933-944, vol. 51, No. 5.
Lopez, A. M., et al., "Systemic administration of 2-hydroxypropyl-b-cyclodextrin to symptomatic Npc1-deficient mice slows cholesterol sequestration in the major organs and improves liver function," Clinical and Experimental Pharmacology and Physiology, 2014, pp. 780-787, vol. 41.
Maarup, T.J., et al, "Intrathecal 2-hydroxypropyl-beta-cyclodextrin in a single patient with Niemann-Pick C1," Molecular Genetics Metababolism, 2015, pp. 75-79, vol. 116.
Maetzel, D., et al., "Genetic and chemical correction of cholesterol accumulation and impaired autophagy in hepatic and neural cells derived from Niemann-Pick Type C patient-specific iPS cells," Stem Cell Reports, 2014, pp. 866-880, vol. 2.
Malanga, M., et al., "'Back to the Future': A New Look at Hydroxypropyl Beta-Cyclodextrins," Journal of Pharmaceutical Sciences, 2016, pp. 2921-2931, vol. 105.
Marcus, A. D., "A Mom Brokers Treatment for Her Twins' Fatal Illness," Wall Street Journal, Apr. 3, 2009, [online] [Retrieved on Jan. 15, 2016] Retrieved from the Internet <URL: http://www.wsj.com/articles/SB123871183055784317>.
Matsuo, M., et al., "Effects of cyclodextrin in two patients with Niemann-Pick Type C disease," Molecular Genetics Metabolism, 2013, pp. 76-81, vol. 108.
Maue, R., et al., "A novel mouse model of Niemann-Pick type C disease carrying a D1005G-Npc1 mutation comparable to commonly observed human mutations," HumAN Molecular Genetics, 2012, pp. 730-750, vol. 21, No. 4.
McCook, A., "Twin Disorders," The Scientist, 2008, pp. 32-38, vol. 22, No. 11.
Mengel, E., et al., "Niemann-Pick disease type C symptomatology: an expert-based clinical description," Orphanet Journal of Rare Diseases, 2013, vol. 8, No. 166, 11 Pages.
Meske, V., et al., "The autophagic defect in Niemann-Pick disease type C neurons differs from somatic cells and reduces neuronal viability," Neurobiology Disease, 2014, pp. 88-97, vol. 64.
Meske, V., et al., "How to reduce the accumulation of autophagic vacuoles in NPC1-deficient neurons: a comparison of two pharmacological strategies," Neuropharmacology, 2015, pp. 282-289, vol. 89.
Millat, G., et al., "Niemann-Pick C1 disease: the I1061T substitution is a frequent mutant allele in patients of Western European descent and correlates with a classic juvenile phenotype," Am. J. Hum. Genet., 1999, pp. 1321-1329, vol. 65.
Müller, B. W., et al., "Solubilization of drugs by modified β-cyclodextrins," International Journal of Pharmaceutics, 1985, pp. 77-88, vol. 26.

Munkacsi, A.B., et al., "An "exacerbate-reverse" strategy in yeast identifies histone deacetylase inhibition as a correction for cholesterol and sphingolipid transport defects in human Niemann-Pick type C disease," The Journal of Biological Chemistry, 2011, pp. 23842-23851, vol. 286, No. 27.
Nah, J., et al., "Autophagy in neurodegenerative diseases: from mechanism to therapeutic approach," Molecules and Cells, 2015, pp. 381-389, vol. 38, No. 5.
NanoSonic Products, Inc. and CTD, Inc., "Certificate of Analysis, Trappsol® THPB-EC," dated Apr. 22, 2015.
Nunes, M.J., et al., "Histone deacetylase inhibition decreases cholesterol levels in neuronal cells by modulating key genes in cholesterol synthesis, uptake and efflux," PloS One, 2013, vol. 8, No. 1, e53394.
Ordonez, P. M., et al., "Disruption and therapeutic rescue of autophagy in a human neuronal model of Niemann Pick type C1," Human Molecular Genetetics, 2012, pp. 2651-2662, vol. 21, No. 12.
Ottinger, E. A., et al., "Collaborative Development of 2-Hydroxypropyl-b-Cyclodextrin for the Treatment of Niemann-Pick Type C1 Disease," Current Topics in Medicinal Chemistry, 2014, pp. 330-339, vol. 14.
Pacheco, C.D., et al., "Autophagy in Niemann-Pick C disease is dependent upon Beclin-1 and responsive to lipid trafficking defects," Human Molecular Genetics, 2007, pp. 1495-1503, vol. 16. No. 12.
Papandreou, A., et al., "Diagnostic workup and management of C patients with suspected Niemann-Pick type C disease," Therapeutic Advances in Neurological Disorders, 2016, pp. 216-229, vol. 9, No. 3.
Patterson, M., "Niemann-Pick Disease Type C," GeneReviews®, 2000, [online][Retrieved on Nov. 10, 2016] Retrieved from the Internet <URL:https://www.ncbi.nlm.nih.gov/books/NBK1296/>.
Patterson, M.C., "Miglustat for treatment of Niemann-Pick C disease: a randomised controlled study," The Lancet Neurology, 2007, pp. 765-772, No. 6.
Patterson, M.C., et al., "Long-term miglustat therapy in children with Niemann-Pick disease type C," Journal of Child Neurology, 2010, pp. 300-305, No. 25, No. 3.
Patterson, M.C., et al., "Recommendations for the diagnosis and management of Niemann-Pick disease type C: an update," Mol. Genet. Metab., 2012, pp. 330-344, vol. 106, No. 3.
Peake, K. B., et al., "Normalization of Cholesterol Homeostasis by 2-Hydroxypropyl-b-cyclodextrin in Neurons and Glia from Niemann-Pick C1 (NPC1)-deficient Mice," J. Biol. Chem., 2012, pp. 9290-9298, vol. 287, No. 12.
Pharmacopeia Online, "Hydroxypropyl Betadex," [online][Retrieved on May 4, 2015] Retrieved from the Internet <URL:http://www.uspbpep.com/usp32/pub/data/v32270/usp32nf27s0_m39130.html>.
Pillai, B. K., et al., "Fast Diffusion of Very Long Chain Saturated Fatty Acids across a Bilayer Membrane and Their Rapid Extraction by Cyclodextrins: Implications for Adrenoleukodystrophy," Journal of Biological Chemistry, 2009, pp. 33296-33304, vol. 284, No. 48.
Pipalia, N.H., et al., "Histone deacetylase inhibitor treatment dramatically reduces cholesterol accumulation in Niemann-Pick type C1 mutant human fibroblasts," Proceedings of the National Academy of Sciences, 2011, pp. 5620-5625, vol. 108, No. 14.
Pitha, J., et al., "Hydroxypropyl-β-cyclodextrin: preparation and characterization; effects on solubility of drugs," International Journal of Pharmaceutics, 1986, pp. 73-82, vol. 29, No. 1.
Pitha, J., et al., "Distribution of substituents in 2-hydroxypropyl ethers of cyclomaltoheptaose," Carbohydrate Research, 1990, pp. 429-435, vol. 200.
Pontikis, C.C., et al., "Cyclodextrin alleviates neuronal storage of cholesterol in Niemann-Pick C disease without evidence of detectable blood-brain barrier permeability," J Inherit Metab Dis, 2013, pp. 491-198, No. 36.
Porter, F. D., et al., "Phase 1/2 evaluation of intrathecal 2-hydroxypropyl-β-cyclodextrin for the treatment of Niemann-Pick disease type C1," Abstract / Molecular Genetics and Metabolism, 2016, p. S97, vol. 117, S14-S124.
Puskása, I., et al., "Aggregation behavior of cyclodextrin and cholesterol in simulated human cerebrospinal fluid," Bioactive Carbohydrates and Dietary Fibre, 2013, pp. 157-163, vol. 2, No. 2.

(56) References Cited

OTHER PUBLICATIONS

Ramirez, C. M., et al., "Weekly Cyclodextrin Administration Normalizes Cholesterol Metabolism in Nearly Every Organ of the Niemann-Pick Type C1 Mouse and Markedly Prolongs Life," Pediatric Research, 2010, pp. 309-315, vol. 68, No. 4.
Ramirez, C. M., et al., "Quantitative role of LAL, NPC2, and NPC1 in lysosomal cholesterol processing defined by genetic and pharmacological manipulations," Journal of Lipid Research, 2011, pp. 688-698, vol. 52, No. 4.
Rao, C. T., et al., "Substitution in beta-cyclodextrin directed by basicity: preparation of 2-O-and 6-O-[(R)-and (S)-2-hydroxypropyl] derivatives," The Journal of Organic Chemistry, 1991, pp. 1327-1329, vol. 56, No. 1.
Rao, C. T., et al., "Distribution of substituents in O-(2-hydroxypropyl) derivatives of cyclomalto-oligosaccharides (cyclodextrins): influence of increasing substitution, of the base used in the preparation, and of macrocyclic size," Carbohydrate Research, 1992, pp. 99-107, vol. 223.
Rauniyar, N., et al., "Quantitative Proteomics of Human Fibroblasts with I1061T Mutation in Niemann-Pick C1 (NPC1) Protein Provides Insights into the Disease Pathogenesis," Molecular & Cellular Proteomics, 2015, pp. 1734-1749, vol. 14, No. 7.
Reagan, J.W., et al., "Posttranslational regulation of acid sphingomyelinase in niemann-pick type C1 fibroblasts and free cholesterol-enriched chinese hamster ovary cells," The Journal of Biological Chemistry, 2000, pp. 38104-38110, vol. 275, No. 48.
Reddy, J.V., et al., "Clues to neuro-degeneration in Niemann-Pick type C disease from global gene expression profiling," PloS One, 2006, No. 1, e19.
Roquette, Brochure: "Kleptose® HP / Kleptose® HPB, multifunctional excipients for molecular encapsulation," 2005, [online][Retrieved on Sep. 16, 2016] Retrieved from the Internet <URL:http://www.roquette-pharma.com/brochures/23/visio.html>.
Roquette, "Kleptose® HPB Parenteral Grade product specification sheet," dated Mar. 2, 2015.
Roquette, "Kleptose® HPB Parenteral Grade product specification sheet," dated Jul. 28, 2014.
Rodal, S. K., et al., "Extraction of Cholesterol with Methyl--Cyclodextrin Perturbs Formation of Clathrin-coated Endocytic Vesicles," Molecular Biology of the Cell, 1999, pp. 961-974, vol. 10.
Rosenbaum, A. I., et al., "Endocytosis of beta-cyclodextrins is responsible for cholesterol reduction in Niemann-Pick type C mutant cells," Proceedings of the National Academy of Sciences, 2010, pp. 5477-5482, vol. 107, No. 12.
Rosenbaum, A. I., et al., "Niemann-Pick type C disease: molecular mechanisms and potential therapeutic approaches," Journal of Neurochemistry, 2011, pp. 789-795, vol. 116, No. 5.
Sarkar, S., et al., "Impaired autophagy in the lipid-storage disorder Niemann-Pick type C1 disease," Cell Report, 2013, pp. 1302-1315, No. 5.
Sarkar, S., et al., "Restarting stalled autophagy a potential therapeutic approach for the lipid storage disorder, Niemann-Pick type C1 disease," Autophagy, 2014, pp. 137-140, vol. 10, No. 6.
Schultz, M. L., et al., "Clarifying lysosomal storage diseases," Trends Neurosci., 2011, pp. 401-410, vol. 34, No. 8.
Soga, M., et al., "HPGCD outperforms HPBCD as a potential treatment for Niemann-Pick disease type C during disease modeling with iPS cells," Stem Cells, 2015, pp. 1075-1088, vol. 33.
Song, W., et al., "2-Hydroxypropyl-β-cyclodextrin Promotes Transcription Factor EB-mediated Activation of Autophagy Implications for Therapy," Journal of Biological Chemistry, 2014, pp. 10211-10222, vol. 289, No. 14.
Swaroop, M., et al., "Evaluation of cholesterol reduction activity of methyl-beta-cyclodextrin using differentiated human neurons and astrocytes," Journal of Biomolecular Screening, 2012, pp. 1243-1251, vol. 17, No. 9.
Szejtli, J., "Medicinal Applications of Cyclodextrins," Medicinal Research Reviews, 1994, pp. 353-386, vol. 14, No. 3.
Tamura, A., et al., "Beta-Cyclodextrin-threaded biocleavable polyrotaxanes ameliorate impaired autophagic flux in Niemann-Pick type C disease," J Biol Chem, 2015, pp. 9442-9454, vol. 290, No. 15.
Thein, P., et al., "In vitro assessment of antiretroviral drugs demonstrates potential for ototoxicity," Hearing Research, 2014, pp. 27-35, vol. 310.
Tortelli, B., et al., "Cholesterol homeostatic responses provide biomarkers for monitoring treatment for the neurodegenerative disease Niemann-Pick C1 (NPC1)," Human Molecular Genetics, 2014, pp. 6022-6033, vol. 23, No. 22.
United States Pharmacopeial Convention, "Hydroxypropyl Betadex," Official Monographs, Dec. 1, 2015, pp. 6692-6695, NF 33.
Vanier, M. T., "Niemann-Pick disease type C," Orphanet Journal of Rare Diseases, 2010, vol. 5, No. 16, 1-18.
Vance, J.E., et al., "Function of the Niemann-Pick type C proteins and their bypass by cyclodextrin," Current Opinion in Lipidology, 2011, pp. 204-209, vol. 22.
Vance, J.E., et al., "Niemann-Pick C disease and mobilization of lysosomal cholesterol by cyclodextrin," Journal of Lipid Research, 2014, pp. 1609-1621, vol. 55.
Vanier, M.T., et al., "Niemann-Pick disease type C," Clinical Genetics, 2003, pp. 269-281, vol. 64.
Vazquez, M.C., et al., "Alteration of gene expression profile in Niemann-Pick type C mice correlates with tissue damage and oxidative stress," PloS One, 2011, vol. 6, No. 12, e28777.
Vieira, C., et al., "Use of Cyclodextrin in Two Brazilian Girls With Niemann-Pick Type C—Intrathecal Report," Jun. 2012, Abstract, [online] [Retrieved on Jul. 20, 2016] Retrieved from the Internet <URL:http://niemannpick.nd.edu/assets/69394/abstracts_in_speaking_order.pdf>.
Vieira, C., "APMRF 2011 meeting summary for NPC families and the NPC community," Jun. 2011, Abstract, [online] [Retrieved on Jul. 20, 2016] Retrieved from the Internet <URL:http://niemannpick.nd.edu/assets/52704/apmrf_2011_summary_for_npc_families_and_the_npc_community.pdf>.
Vieira, C., "The use of Cyclodextrin in Niemann-Pick Type C disease in two girls Report after one year of treatment," Jun. 2011, Abstract, [online] [Retrieved on Jul. 20, 2016] Retrieved from the Internet <URL:http://niemannpick.nd.edu/assets/52702/all_abstracts.pdf>.
Vite, C. H., et al., "Clinical, electrophysiological, and serum biochemical measures of progressive neurological and hepatic dysfunction in feline Niemann-Pick type C disease," Pediatric Research, 2008, pp. 544-549, vol. 64, No. 5.
Vite, C. H., et al., "Intracisternal cyclodextrin prevents cerebellar dysfunction and Purkinje cell death in feline Niemann-Pick type C1 disease," Science Translational Medicine, 2015, vol. 7, No. 276, 1-16.
Vite, C., et al., "Intrathecal cyclodextrin therapy of feline Niemann-Pick Type C disease" (Abstract) Molecular Genetics and Metabolism 102(2011), S3-S47.
Vtesse, Inc., "Leading Life Science Syndicate Commits $25 Million to Series A Funding to Launch Vtesse, Inc., the First Rare Disease Company Spun Out of Cydan Development, Vtesse to collaborate with National Institutes of Health on development of VTS-270 for Niemann-Pick Disease Type C and other novel drugs for life-threatening rare diseases," Jan. 7, 2015, Press Release, [online][Retrieved Jul. 20, 2016] Retrieved from the Internet <URL:http://www.vtessepharma.com/2015jan07-leading-life-science-syndicate>.
Vtesse, Inc., "NIH teams with industry to develop treatments for Niemann-Pick Type C disease.," Jan. 7, 2015, Press Release, [online][Retrieved on Sep. 16, 2016] Retrieved at <URL:https://www.nih.gov/news-events/news-releases/nih-teams-industry-develop-treatments-niemann-pick-type-c-disease>.
Vtesse, Inc., "Small Biotech Gets Rights to Rare Disease Drug," Jan. 7, 2015, Press Release, [online][Retrieved on Sep. 16, 2016] Retrieved at <URL:http://www.wsj.com/articles/small-biotech-vtesse-gets-rights-to-rare-disease-drug-1420606861>.
Vtesse, Inc., "Vtesse, Inc. Forms Scientific Advisory Board " Mar. 25, 2015, Press Release, [online][Retrieved on Sep. 16, 2016] Retrieved at <URL:http://www.vtessepharma.com/2015mar25-vtesse-forms-scientific-adviso>.

(56) References Cited

OTHER PUBLICATIONS

Vtesse, Inc., "Vtesse, Inc. Expands Scientific Advisory Board, Fills Key Patient Advocacy Position to Prepare for Further Clinical Development of VTS-270 in Niemann-Pick Disease Type C (NPC)," Jun. 15, 2015, Press Release, [online][Retrieved on Jul. 20, 2016] Retrieved from the Internet <URL:http://www.vtessepharma.com/2015jun15-vtesse-inc-expands-scientifi.

Vtesse, Inc., "Vtesse, Inc. Announces Preliminary Data from Ongoing Phase 1 Study of VTS-270 for Treatment of Niemann-Pick Disease Type C," Aug. 6, 2015, Press Release, [online][Retrieved on Jul. 20, 2016] Retrieved from the Internet <URL:http://www.vtessepharma.com/2015aug06-vtesse-inc-announces>.

Vtesse, Inc., "Vtesse, Inc. Initiates Phase 2b/3 Clinical Trial of VTS-270 for Treatment of Niemann-Pick Type C1 (NPC) Disease," Sep. 28, 2015, Press Release, [online][Retrieved on Jul. 20, 2016] Retrieved from the Internet <URL:http://www.vtessepharma.com/2015sep28-initiates-phase-2b3-clinical->.

Vtesse, Inc., "Vtesse, Inc. Expands Scientific Advisory Board and Appoints New VP of Clinical Operations to Support Late-Stage Clinical Study of Lead Drug Candidate VTS-270," Oct. 22, 2015, Press Release, [online][Retrieved on Jul. 20, 2016] Retrieved from the Internet <URL:http://www.vtessepharma.com/2015oct22-vtesse-inc-expands-scientifi>.

Vtesse, Inc., "Vtesse, Inc. Announces FDA's Granting of Breakthrough Therapy Designation for VTS-270 in Niemann-Pick Type C1 Disease," Jan. 6, 2016, Press Release, [online][Retrieved on Jul. 20, 2016] Retrieved at <URL:http://www.vtessepharma.com/blank>.

Vtesse, Inc., "Vtesse, Inc. Announces Phase 1/2 Clinical Data Showing Slowing of Disease Progression from VTS-270 Treatment for Niemann-Pick Type C1 Disease," Mar. 4, 2016, Press Release, [online][Retrieved on Jul. 20, 2016] Retrieved at <http://www.vtessepharma.com/blank-1>.

Vtesse, Inc., "Vtesse Advances Phase 2b/3 Clinical Trial of VTS-270 in Niemann-Pick Type C1 Disease with Dose Selection for Evaluation in Second and Final Portion of Trial and Expansion into Europe," May 23, 2016, Press Release, [online][Retrieved on Jul. 1, 2016] Retrieved from the Internet <URL:http://www.vtessepharma.com/2016may23-press-release>.

Vtesse, Inc., "Vtesse Secures Additional $17 Million in Series A Extension to Support Further Product Development and Expand the Ongoing Clinical Trial of VTS-270 for the Treatment of Niemann-Pick Type C1 Disease," Jul. 25, 2016, Press Release, [online][Retrieved on Sep. 16, 2016] Retrieved from the Internet <URL:http://www.vtessepharma.com/july25-press-release>.

Walkley, S. U., "Cellular Pathology of lysosomal storage disorders," Brain Pathology, 1998, pp. 176-190, vol. 8.

Walkley, S. U., et al., "Gangliosides as modulators of dendritogenesis in normal and storage disease-affected pyramidal neurons," Cerebral Cortex, 2000, pp. 1028-1037, vol. 10, No. 10.

Walkley, S., et al., "141. Cyclodextrin treatment not only delays but also reduces established intraneuronal storage in Niemann-Pick type C disease," (Abstract), Molecular Genetics and Metabolism, 2010, p. S37, vol. 99, No. 2.

Walkley, S. U., et al., "Lysosomal compromise and brain dysfunction: examining the role of neuroaxonal dystrophy," Biochemical Society Transactions, pp. 1436-1442, 2010, vol. 38, No. 6.

Walkley, S. U. et al., "Consequences of NPC1 and NPC2 loss of function in mammalian neurons," Biochemica et Physica Acta (BBA), Molecular and Cell Biology of Lipids, 2004, 2685(1-3), pp. 48-62.

Wang, M. L., "Identification of Surface Residues on Niemann-Pick C2 (NPC2) Essential for Hydrophobic Handoff of Cholesterol to NPC1 in Lysosomes," Cell Metab., 2010, 12(2): 166-173.

Ward, S., et al., "2-hydroxypropyl-β-cyclodextrin raises hearing threshold in normal cats and in cats with Niemann-Pick type C disease," Pediatric Research, 2010, pp. 52-56, vol. 68, No. 1.

Wehrmann, Z.T., et al., "Quantitative comparison of the efficacy of various compounds in lowering intracellular cholesterol levels in Niemann-Pick type C fibroblasts," PloS One, 2012, vol. 7, No. 10, e48561.

Wraith, J.E., et al., "Miglustat in adult and juvenile patients with Niemann-Pick disease type C: long-term data from a clinical trial," Molecular Genetics and Metabolism, 2010, pp. 351-357, vol. 99.

Xu, M., et al., "δ-Tocopherol reduces lipid accumulation in Niemann-Pick type C1 and Wolman cholesterol storage disorders," Journal of Biological Chemistry, 2012, pp. 39349-39360, vol. 287, No. 47.

Xu, M., et al., "A phenotypic compound screening assay for lysosomal storage diseases," Journal of Biomolecular Screening, 2014, pp. 168-175, vol. 19, No. 1.

Yanjanin, N. M., "Linear clinical progression, independent of age of onset, in Niemann-Pick disease, type C," American Journal of Medical Genetics Part B: Neuropsychiatric Genetics, 2010, pp. 132-140, vol. 153, No. 1.

Yergey, A. L., et al., Poster: "Characterization of Hydroxypropyl-Beta-Cyclodextrins by ESI Ion Mobility Mass Spectrometry," Michael, Marcia, and Christa Parseghian Scientific Conference for Niemann-Pick Type C Research, Tucson, Arizona, Jun. 11-13, 2016.

Yergey, A.L. et al., "Characterization of Hydroxypropyl-Beta-Cyclodextrins Used in the Treatment of Niemann-Pick Disease Type C1," PLOS One, Apr. 17, 2017, pp. 1-13.

Yu, D., et al., "Niemann-Pick Disease Type C: Induced Pluripotent Stem Cell-Derived Neuronal Cells for Modeling Neural Disease and Evaluating Drug Efficacy," Journal of Biomolecular Screening, 2014, pp. 1164-1173, vol. 19, No. 8.

Yuan, C., et al., "Characterization of hydroxypropyl-β-cyclodextrins with different substitution patterns via FTIR, GC-MS, and TG-DTA," Carbohydrate Polymers, 2015, pp. 36-40, vol. 118.

Zervas, M., et al., "Critical role for glycosphingolipids in Niemann-Pick disease type C," Current Biology, 2001, pp. 1283-1287, vol. 11.

Office action dated Apr. 5, 2019 from related Australian Application No. 2018202964, 9 pp.

Office action dated Mar. 27, 2019 from related European Application No. 13762617.2, 4 pp.

Hackman, Translation of Research Evidence From Animals to Humans, J Am Med Assoc (JAMA), 2006, vol. 296, No. 14, pp. 1731-1732.

Mak, Lost in translation: animal models and clinical trials in cancer treatment, Am J Transl Res, 2014, vol. 6(2), pp. 114-118.

Perlman, Mouse models of human disease, An evolutionary perspective, Evolution, Medicine, and Public Health, 2016, pp. 170-176.

Stella, Cyclodextrins, Toxicologic Pathology, 2008, vol. 36, pp. 30-42.

Notice of Acceptance dated Aug. 8, 2019 from related Australian Application No. 2018202964, 3 pp.

Office action dated Aug. 23, 2019 from related Canadian Application No. 2,880,880, 5 pp.

Office action dated Jun. 10, 2019 from related Japanese Application No. 2018-116666, 5 pp.

Office action dated Oct. 23, 2019 from related Japanese Application No. 2018-116666, 2 pp.

Office action dated Jul. 1, 2020 from related CN Application No. 201711057517.4, 9 pp.

Liu, "Therapeutic potential of Cyclodextrins in the treatment of Niemann-Pick type C disease," Clin Lipidol., Jun. 2012, 7(3): 289-301.

\* cited by examiner

LYSOTRACKER STAINING IN MLIV (8 MONTH)

LYSOTRACKER STAINING IN MPSI

CYCLODEXTRIN FOR THE TREATMENT OF LYSOSOMAL STORAGE DISEASES

RELATED APPLICATIONS

This application claims priority of U.S. Provisional Application No. 61/679,668, filed on Aug. 3, 2012, the entirety of which is incorporated by reference herein.

This application is a continuation of U.S. application Ser. No. 14/419,471, filed Feb. 3, 2015, which is the National Stage of International Application PCT/US2013/053527, filed Aug. 3, 2013, which claims priority of U.S. Provisional Application No. 61/679,668, filed on Aug. 3, 2012, each of which is incorporated by reference herein.

FEDERALLY SPONSORED RESEARCH

This work was supported by the Federal Government. The Government has certain rights in this invention.

TECHNICAL FIELD

The invention provides for methods of treating lysosomal storage disorders and/or reduction of non-cholesterol lipids, using cyclodextrin compounds and cyclodextrin compounds in combination with other agents.

BACKGROUND OF THE INVENTION

Cyclodextrins (CD) are sugar molecules in a ring form. The alpha-CD (6 sugars), beta-CD (7 sugars) and gamma-CD (8 sugars) are commonly used cyclodextrins. The hydroxypropyl-beta cyclodextrin (HPβCD) has been approved for the pharmaceutical use as the drug excipient. Recent reports showed that beta-cyclodextrin including HPβCD and beta-methyl-cyclodextrin (MβCD) reduced cholesterol accumulation and neuronal cell loss in the mouse model of Niemann Pick Type C (NPC) disease. The life span of these NPC KO mice also increased 80 to 100% after the CD treatment. The similar positive results were obtained in the feline model of NPC disease. It was also reported that beta-CD increased exocytosis in primary NPC fibroblasts.

It has been recently found that delta-tocopherol increased the cholesterol efflux from NPC cells and reduced cholesterol accumulation. Enhancement of lysosomal exocytosis has been indicated as a therapeutic strategy for development of new treatment for all lysosomal storage diseases that are composed of 50 different diseases caused by the genetic mutations of genes for lysosomal proteins. The phenotypic changes in these diseases are accumulation of lipids, glycoprotein and/or other macromolecules in lysosomes and enlarged lysosome size in patient cells that may lead to cell malfunction and cell death in affected tissues.

SUMMARY OF THE INVENTION

In one aspect, the invention provides a method of treating a lysosomal storage disorder in a subject, comprising determining that the subject is in need of non-cholesterol lipid reduction or reduction of non-cholesterol dominant lipid and macromolecule accumulation, and administering to the subject in need thereof, an effective amount of a cyclodextrin compound, or a pharmaceutically acceptable salt, ester, solvate or hydrate thereof.

In another aspect, the invention provides a method treating a lysosomal storage disorder in a subject, wherein the subject has been previously identified as being in need of non-cholesterol lipid reduction or reduction of non-cholesterol dominant lipid and macromolecule accumulation, comprising administering to said subject in need thereof an effective amount of a cyclodextrin compound, or a pharmaceutically acceptable salt, ester, solvate or hydrate thereof.

In another aspect, the invention provides a method of treating a lysosomal storage disorder in a subject, comprising the step of administering to the subject an effective amount of a cyclodextrin compound, or a pharmaceutically acceptable salt, ester, solvate or hydrate thereof, and an additional therapeutic agent.

In certain aspects, the invention provides a method of reducing non-cholesterol lipids or reduction of non-cholesterol dominant lipid and macromolecule accumulation in a subject, the method comprising administering to the subject a cyclodextrin compound, or a pharmaceutically acceptable salt, ester, solvate or hydrate thereof; and detecting the amount of lipid reduction.

In another aspect, the invention provides a pharmaceutical composition comprising a cyclodextrin compound, or a pharmaceutically acceptable salt, ester, solvate or hydrate thereof, and vitamin E, together with a pharmaceutically-acceptable carrier or excipient.

In another aspect, the invention provides a method of treating a subject suffering from a lysosomal storage disorder, comprising the use of the pharmaceutical composition as described above, in combination with another agent.

In one embodiment of any of the above aspects, the step of administering the cyclodextrin compound comprises administering the cyclodextrin compound to a subject such as a human in a dosage of between about 0.01 mg/Kg/day and 100 mg/Kg/day.

In another embodiment of any of the above aspects, the cyclodextrin compound is administered to a subject such as a human in an amount from about 0.5 mg/Kg to 8 mg/Kg, either in a single dose or per day.

In one embodiment of any of the above aspects, the cyclodextrin compound is administered to a subject such as a human in an amount of about 3 mg/Kg either in a single dose or per day. In a further embodiment of any one of the above aspects, the cyclodextrin compound is administered to a subject such as a human in an amount of about 1.0 mg/Kg, 1.25 mg/Kg, 1.5 mg/Kg, 1.75 mg/Kg, 2.0 mg/Kg, 2.25 mg/Kg, 2.5 mg/Kg, 2.75 mg/Kg, 3.25 mg/Kg, 3.5 mg/Kg, 3.75 mg/kg, 4.0 mg/Kg, 4.25 mg/Kg, or 4.5 mg/kg, either in a single dose or per day.

In another further embodiment of any of the above aspects, the cyclodextrin compound is administered to a subject such as a human in an amount from about 0.1 mg/Kg, to 0.3 mg/Kg, 0.1 mg/Kg to 0.4 mg/Kg, 0.1 mg/Kg to 0.5 mg/Kg, 0.1 mg/Kg to 0.6 mg/Kg, or 0.1 mg/Kg to 0.7 mg/Kg, either in a single dose or per day.

In another further embodiment of any of the above aspects, the cyclodextrin compound is administered in a single dose.

In one embodiment of any of the above aspects, the additional therapeutic agent (distinct from the cyclodextrin compound) is administered to a subject such as a human in an amount from about 0.05 to 1 mg/kg, either in a single dose or per day. In another embodiment of any of the above aspects, the additional therapeutic agent (distinct from the cyclodextrin compound) is administered to a subject such as a human in an amount from about 0.1 mg/Kg to 0.3 mg/Kg, 0.1 mg/Kg to 0.4 mg/Kg, 0.1 mg/Kg to 0.5 mg/Kg, 0.1 mg/Kg to 0.6 mg/Kg, or 0.1 mg/Kg to 0.7 mg/Kg, either in a single dose or per day.

In one embodiment of any of the above aspects, the additional therapeutic agent is administered in a single dose.

In another aspect, the invention features a method of treating a lysosomal storage disorder in a subject, comprising determining that the subject is in need of non-cholesterol lipid reduction or reduction of non-cholesterol dominant lipid and macromolecule accumulation; administering to the subject in need thereof, an effective amount of a cyclodextrin compound, or a pharmaceutically acceptable salt, ester, solvate or hydrate thereof in an amount from about 0.05 mg/Kg to 1 mg/Kg either in a single dose or per day; and administering to the subject an additional therapeutic agent (such as vitamin E) distinct from the cyclodextrin compound in an amount from about 0.005 mg/Kg to 1 mg/Kg either in a single dose or per day.

In another aspect, the invention features a method of treating a lysosomal storage disorder in a subject, comprising determining that the subject is in need of non-cholesterol lipid reduction or reduction of non-cholesterol dominant lipid and macromolecule accumulation; administering to the subject in need thereof, an effective amount of a cyclodextrin compound, or a pharmaceutically acceptable salt, ester, solvate or hydrate thereof; and administering to the subject an additional therapeutic agent (such as vitamin E) distinct from the cyclodextrin compound.

In one embodiment the cyclodextrin compound is administered to a subject such as a human in an amount from about 0.1 mg/Kg, to 0.3 mg/Kg, 0.1 mg/Kg to 0.4 mg/Kg, 0.1 mg/Kg to 0.5 mg/Kg, 0.1 mg/Kg to 0.6 mg/Kg, or 0.1 mg/Kg to 0.7 mg/Kg, either in a single dose or per day.

In another embodiment, the additional therapeutic agent (distinct from the cyclodextrin compound) is administered to a subject such as a human in an amount from about 0.1 mg/Kg, to 0.3 mg/Kg, 0.1 mg/Kg to 0.4 mg/Kg, 0.1 mg/Kg to 0.5 mg/Kg, 0.1 mg/Kg to 0.6 mg/Kg, or 0.1 mg/Kg to 0.7 mg/Kg, either in a single dose or per day.

In still another further embodiment, the cyclodextrin compound is administered to a subject such as a human in an amount of about 50 μM in combination with 10 μM of an additional agent, either in a single dose or per day.

In a further preferred embodiment, the cyclodextrin compound is administered to a subject such as a human in an amount of about 50 μM in combination with 10 μM of delta-tocopherol, either in a single dose or per day.

In other aspects, the invention provides a kit comprising an effective amount of a cyclodextrin compound, or a pharmaceutically acceptable salt, ester, solvate or hydrate thereof, in unit dosage form, together with instructions for administering the compound to a subject suffering from a lysosomal storage disorder.

Various advantages of the invention include the following: Treatment of all lysosomal storage diseases with cyclodextrins, including hydroxypropyl-beta-cyclodextrin, but in certain aspects with the exception of Niemann Pick Type C disease; treatment of all lysosomal storage diseases with cyclodextrins, including hydroxypropyl-beta-cyclodextrin in combination of vitamin-E, for synergistic or additive therapeutic effect, for reduction of dosage of cyclodextrin needed that makes the cyclodextrin treatment more practically feasible, and for less side effects by reducing dosages of both drugs; treatment of all lysosomal storage diseases with cyclodextrins (such as beta and gama forms) in combination with modified cyclodextrins for better efficacy and less side effects; treatment of all lysosomal storage diseases with cyclodextrins and modified vitamin-E analogs for the better efficacy and less side effects.

Further, the invention provides the administration of the compounds of the invention for the treatment of all 40-50 lysosomal storage diseases based on the mechanism of action of cyclodextrin (increases lysosomal exocytosis).

Other aspects of the invention are disclosed infra.

DETAILED DESCRIPTION

Methods of Treatment

Figure 1:
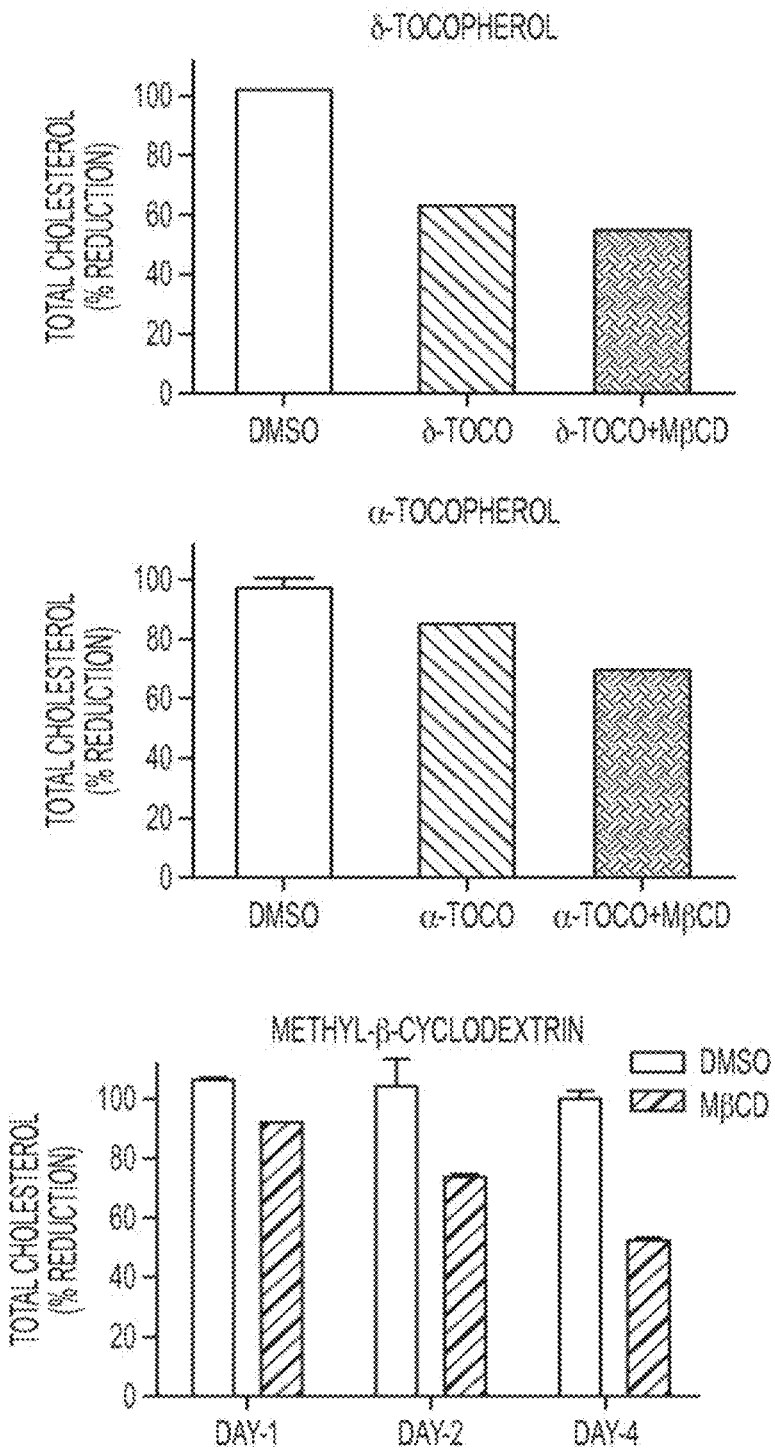
FIG. 1 is a set of graphs showing the reduction of total cholesterol (including cholesterol ester and free cholesterol) in Wolman fibroblasts treated with δ-tocopherol, α-tocopherol, methyl-β-cyclodextrin, and combinations of δ-tocopherol and methyl-β-cyclodextrin, and α-tocopherol and methyl-β-cyclodextrin (MBCD).
Figure 1:
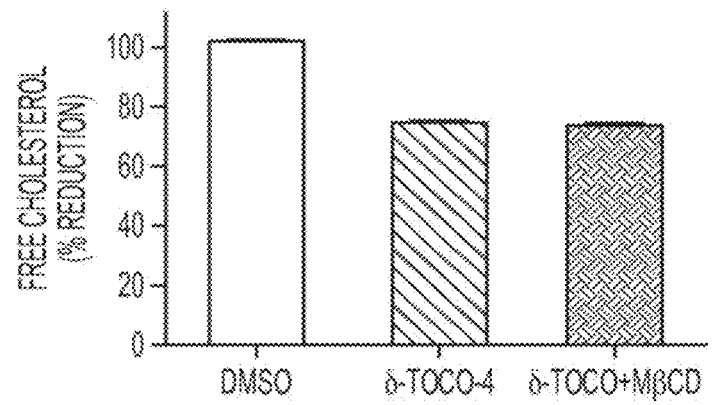
Figure 1:
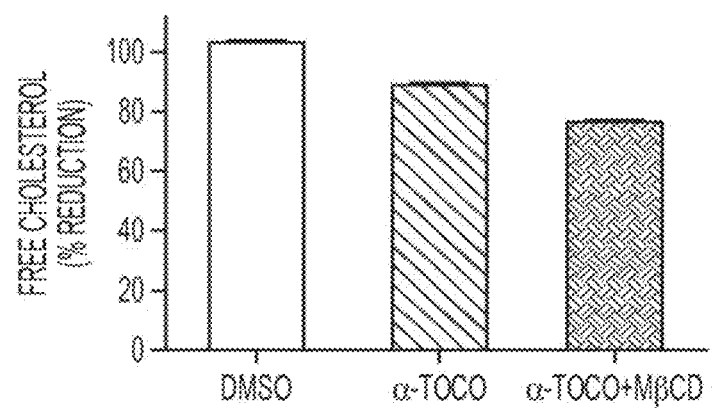
Figure 1:
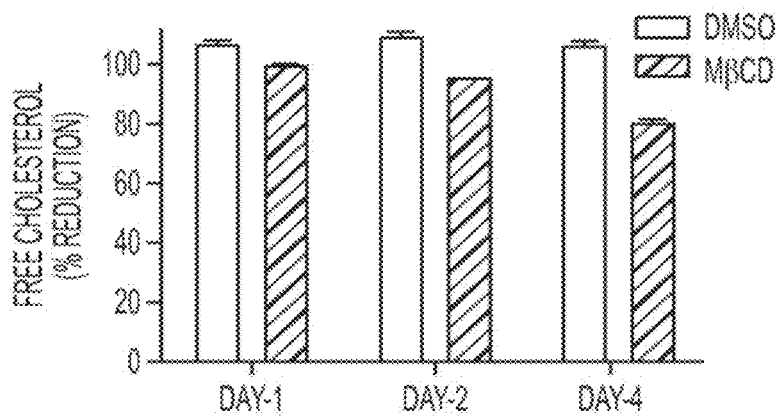

In one aspect, the invention provides a method of treating a lysosomal storage disorder in a subject, comprising determining that the subject is in need of non-cholesterol lipid reduction or reduction of non-cholesterol dominant lipid and other macromolecule accumulation, and administering to the subject in need thereof, an effective amount of a cyclodextrin compound, or a pharmaceutically acceptable salt, ester, solvate or hydrate thereof.

In another aspect, the invention provides a method of treating a lysosomal storage disorder in a subject, wherein the subject has been previously identified as being in need of non-cholesterol lipid reduction or reduction of non-cholesterol dominant lipid and other macromolecule accumulation, comprising administering to said subject in need thereof an effective amount of a cyclodextrin compound, or a pharmaceutically acceptable salt, ester, solvate or hydrate thereof.

In one embodiment, the lysosomal storage disorder is treated by reducing the non-cholesterol lipid or non-cholesterol dominant lipid and other macromolecule accumulation in the subject.

In another embodiment, the non-cholesterol lipid is lipopigments, globotriaosylceramide, ceramide, sphingomyelin, heparan sulfate, partially degraded heparan sulfate, GM2 ganglioside, triglycerides, or cholesterol esters. The other macromolecules include proteins, glycoproteins (sugar containing proteins), mucopolysaccharides (long unbranched polysaccharides), and other cellular components.

A subject may be identified as having a lysosomal storage disease by presenting to a clinician with symptoms of a lysosomal storage disease, including but not limited to an enlarged liver and spleen. Storage may begin during early embryonic development, and the clinical presentation for lysosomal storage diseases can vary from an early and severe phenotype to late-onset mild disease. Said subject may be subject to a variety of diagnostic tests to determine if the subject has a lysosomal storage disease, and further to determine the presence of non-cholesterol lipids and macromolecules and non-cholesterol dominant lipids (i.e. non-cholesterol lipids that are present in an amount or percentage greater than that of cholesterol).

For example, ultrastructural examinations of skin biopsy specimens can be used to detect lysosomal accumulation of undegraded metabolites. A test of specific lysosomal enzyme activity can also be used to determine the presence of specific lysosomal enzymes. Moreover, correlation of both skin ultrastructure and assay for specific lysosomal enzymes in cultured dermal fibroblasts derived from the skin biopsy may also facilitate determination of cholesterol and non-cholesterol lipids, and diagnostic accuracy. Filipin staining is a well-known histochemical stain for cholesterol. Filipin is highly fluorescent and binds specifically to cholesterol. This method of detecting cholesterol in cell membranes is used clinically, for example in the study and diagnosis of Type C Niemann-Pick disease. Molecular genetic testing can be used, may be use to refine the enzymatic diagnosis. Other diagnostic methods to determine the present of cholesterol and non-cholesterol lipids include antibody immunostaining or mass spectrometry.

Lysosomal storage disorders include ~40 to 50 inherited metabolic disorders caused by defects in lysosomal function. The incidence is about 1:5000-1:10,000 as a group of diseases. The term lysosomal refers to a recycling center in which cell membrane and other materials break down to small molecules for reuse. It has been found that deficiency of a single enzyme or proteins required for the metabolism or trafficking of lipids, glycoproteins and other macromolecules results in lipid accumulation in lysosome of cells. Excessive amount of lipids or other materials in lysosome causes enlargement of liver and spleen. Symptoms of neuronal degeneration are common clinical manifestations in patients with neuronal involvements.

Lysosomal storage disorders treated by the invention include, but are not limited to the following: Aspartylglucosaminuria, Wolman disease, Cystinosis, Danon disease, Fabry disease, Farber disease, Fucosidosis, Gaucher disease, GM1-Gangliosidosis types I/II/III, GM2-Gangliosidosis, alpha-Mannosidosis types I/II, beta-Mannosidosis, Metachromatic leukodystrophy, Sialidosis types I/II, Mucolipidosis type IV, Scheie syndrome, Hunter syndrome, Sanfilippo syndrome A, Sanfilippo syndrome B, Sanfilippo syndrome C, Sanfilippo syndrome D, Galactosialidosis types I/II, Krabbe disease, Sandhoff disease, Vogt-Spielmeyer disease, Hurler syndrome, Niemann-Pick disease, I-cell disease (mucolipidosis II), pseudo-Hurler polydystrophy, Morquio syndrome, Maroteaux-Lamy syndrome, Sly syndrome, Mucopolysaccharidosis type IX, Multiple sulfatase deficiency, Batten disease. Tay-Sachs disease, Pompe disease, Batten disease, Batten disease, late infantile, Northern Epilepsy, Pycnodysostosis, Schindler disease, Sialuria, and Salla disease.

In certain embodiments, the lysosomal storage disorder is Tay-Sachs disease, Sphingolipidoses, Gaucher disease, Mucolipidosis, Galactosialidosis, Salla disorder, Cystinosis, Danon disease, Fabry disease, Farber disease, Lipofuscinosis, Pompe disease, Gangliodisosis, ISSD, Krabbe disease, leukodystrophy, Hurler disease, Scheie disease, Hunter disease, San Filippo disease, Sandhoff disease, Schinder disease, Batten disorder, or Wolman disease.

In a further embodiment, the lysosomal storage disorder is Tay-Sachs disease, Fabry disease, Farber disease, San Filippo disease, Batten disorder, or Wolman disease.

In certain embodiments, the cyclodextrin compound is of formula (I):

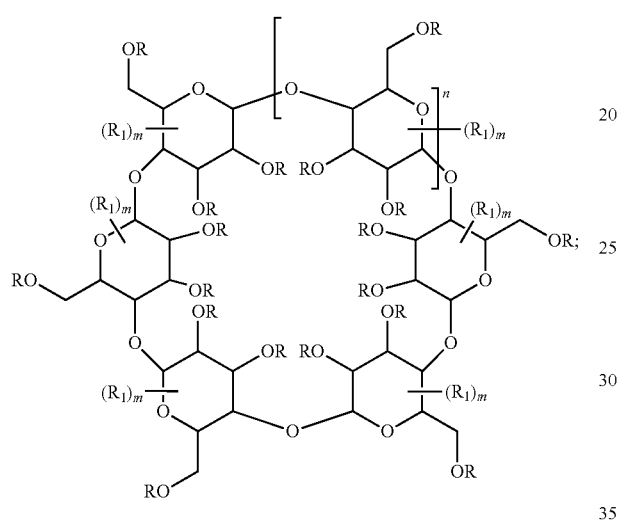

(I)

or a pharmaceutically acceptable salt, ester, solvate or hydrate thereof, wherein, each R is independently H, alkyl, alkenyl, alkynyl, cycloalkyl, heterocycloalkyl, aryl, or heteroaryl, each of which is optionally substituted; or —C(O)OR$^B$, —OC(O)R$^B$, —C(O)R$^B$, or —C(O)NR$^A$R$^B$;

each $R_1$ is independently H, alkyl, alkenyl, alkynyl, cycloalkyl, aryl, heteroaryl, halogen, hydroxy, amino, —CN, —CF$_3$, —N$_3$, —NO$_2$, —OR$^B$, —SR$^B$, —SOR$^B$, —SO$_2$R$^B$, —N(R$^B$)S(O$_2$) —R$^B$, —N(R$^B$) S(O$_2$)NR$^A$R$^B$, —C(O)OR$^B$, —C(O)R$^B$, —C(O)NR$^A$R$^B$, or —N(R$^B$)C(O)R$^B$; each of which is optionally substituted;

each $R^A$ is independently hydrogen, alkyl, alkenyl, alkynyl, cycloalkyl, heterocycloalkyl, aryl, or heteroaryl, each of which is optionally substituted;

Each $R^B$ is independently hydrogen, alkyl, alkenyl, alkynyl, cycloalkyl, heterocycloalkyl, aryl, or heteroaryl, each of which is optionally substituted;

n is 1, 2, 3, 4, 5, 6, 7, 8, 9, or 10; and each m is independently 0, 1, 2, 3, 4, or 5.

In certain embodiments each R is independently H, optionally substituted alkyl, —C(O)OR$^B$, —OC(O)R$^B$, —C(O)R$^B$, or —C(O)NR$^A$R$^B$.

In a further embodiment, each R is independently H, methyl, ethyl, propyl, butyl, pentyl, hexyl, heptyl, or octyl; wherein each is straight chain or branched.

In other embodiments, n is 1, 2, or 3.

In another embodiment, the cyclodextrin is 2-hydroxypropyl-β-cyclodextrin (2HPβCD), hydroxypropyl-β-cyclodextrin (HPβCD), methyl-β-cyclodextrin (MβCD), α-cyclodextrin, β-cyclodextrin, or γ-cyclodextrin, or a pharmaceutically acceptable salt, ester, solvate or hydrate thereof.

In certain embodiments, the compound is:

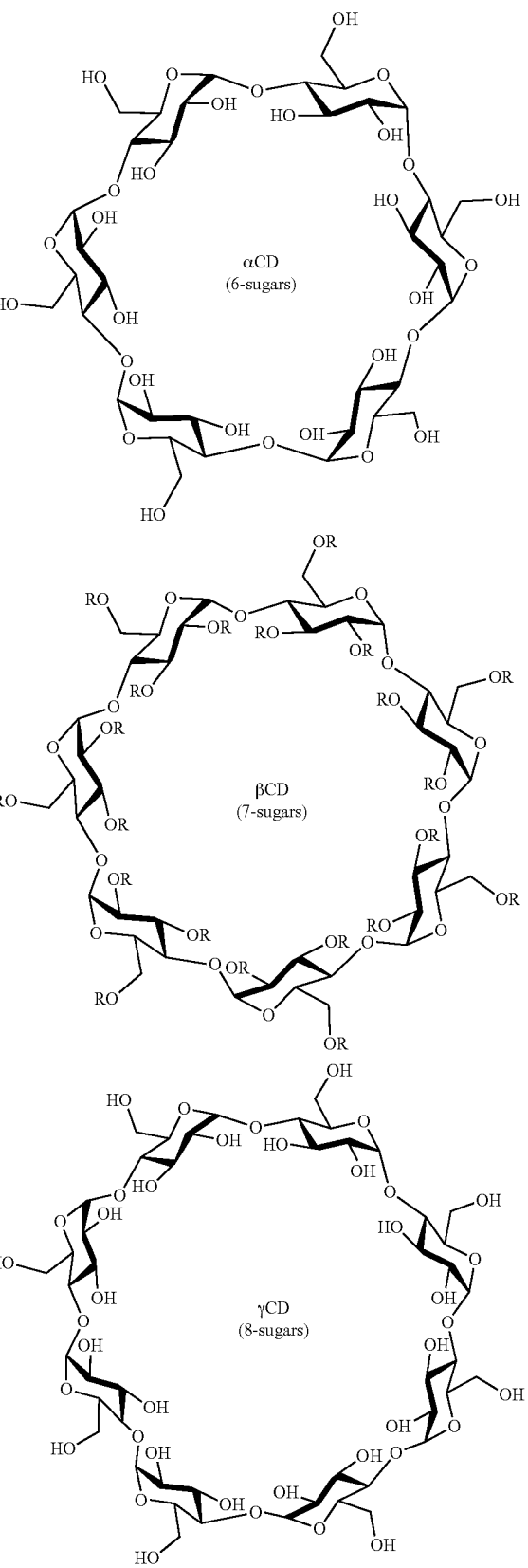

TABLE 1

Types of beta-cyclodextrins

| Name | # of sugars | R | # of R2 | Name |
|---|---|---|---|---|
| Heptakis(2,6-di-o-methyl)-beta-cyclodextrin | 7 | a combination of R1 = —H in position 3 and R2 = —Me in positions 2 and 6 | 14 | MβCD |
| (2-Hydroxypropyl)-beta-cyclodextrin | 7 | a random combination of R1 = —H and R2 = —CH—CHOH—CH3 | 1 to 10 being 4 the most abundant species | Kleptose |
| (2-Hydroxypropyl)-beta-cyclodextrin | 7 | a random combination of R1 = —H and R2 = —CH—CHOH—CH3 | 4-10 being 7 the most abundant species | Trappsol |

In certain embodiments, the step of determining non-cholesterol lipid reduction or non-cholesterol dominant lipid and macromolecule accumulation in a subject comprises any one or more of the following.

Amplex-Red Cholesterol Assay—Total cholesterol in patient cells was measured by the Amplex-Red Cholesterol Assay Kit (Invitrogen). The unesterified cholesterol was determined using the same kit without the enzyme acid lipase. Esterified cholesterol was determined as the difference between the total and unesterified cholesterol values. The cells were seeded to black, tissue culture-treated 96-well, 384-well or 1536-well plates at 4000, 1000, 300 cells/well in 100, 20 or 5 µl medium by a Multidrop Combi dispenser (Thermo Scientific, Waltham, Mass.) and cultured for 24 hr. The assay plates were added with compound dilution in DMSO solution using a Pintool station (Klaypsys, San Diego, Calif.) and cultured for 3 days. The cells were washed twice manually for 96-well or 384-well plates or using a centrifugation method in which the inverted plates were placed on a stack of paper towel and centrifuged at 800 rpm for 1 min followed by addition of 7 µl/well PBS (added gently with a 45 degree angled liquid dispenser (Klaypsys). The cholesterol assay mixture from the kit was added at 100, 20 or 2.5 µl/well for 96-well, 384-well or 1536-well plates and incubated for 1 hr at 37° C. The resulted fluorescence intensity was measured with excitation of 560 (±10) and emission of 590 (±10) in a fluorescence plate reader (Tecan, Durham, N.C.).

Nile-red Staining—The cells were cultured and treated as described above in 96-well plates. On the experimental day, cells were washed two times with PBS and live-stained with 1 µM Nile-red dye solution (prepared in cell culture medium) at 100 µl/well followed by an incubation at 37° C. for 10 min. After washed twice with PBS, the cells were fixed in 3.2% paraformaldehyde in PBS at 100 µl/well 1 µg/ml Hoechst 33342 (Invitrogen) in PBS and incubation at RT for 30 min. The plate was washed twice with PBS and the images were measured in Incell2000 imaging plate reader with a FTTC filter set (Ex=480±20 nm and Ex=525±36 nm) for the neutral lipids (cholesteryl esters and triglycerides) and a DAPI filter set for Hoechst nuclear staining.

LysoTracker Dye Staining—The assay was optimized to visualize the enlarged lysosomes by applying appropriate concentration of LysoTracker dye in which the control cells exhibited minimal staining while the disease cells showed significant staining. The cells were cultured and treated as described above in 96-well plates. On the experimental day, cells were live-stained with 100 µl/well 50 nM LysoTracker-Red DND-99 dye (Invitrogen, #L-7528) in medium at 37° C. for 1 hr followed by plate washing twice with PBS. The plate was then fixed in 100 µl/well 3.2% formaldehyde for 1 hr and washed for two times with PBS. The nuclear staining were carried out by an addition of 100 µl/well 1 µg/ml Hoechst 33342 (Invitrogen) in PBS and incubation at RT for 30 min. After washing twice with PBS, the plates were stored at 4° C. until imaging analysis. DAPI filter set and TRITC filter set in the Incell2000 imaging plate reader were used to visualize Hoechst nuclear staining and LysoTracker staining, respectively.

Measurement of β-Hexosaminidase (HEXB) Release—Fibroblasts were cultured in 24-well plates at 30,000 cells/well in 0.4 ml medium for one day at 37° C. After being washed twice with the assay buffer (DMEM with 2 mM D-mannose 6-phosphate sodium salt), the cells with 0.4 ml/well the assay buffer were incubated at 37° with 0.2 ml/well compound in assay buffer. At the 5, 10, 20, 30 and 40 min time points, 30 µl of assay buffer from each well in the 24-well plate were aliquoted into a 96-well black plate. The rest of assay buffer in the 24-well plate was discarded followed by addition of 0.6 ml 1% Triton-X100 in dH$_2$O to lyse the cells. After incubation at 37° C. for 30 min. 6 µl/well cell lysate were added to the 96-well plate with 24 µl assay buffer followed by 90 µl/well 2.25 mM HEXB substrate, 4-Methylumbelliferyl N-acetyl-β-D-glucosaminide (Sigma-Aldrich, #M2133), in a 25 mM citric acid buffer at pH 4.5. The 96-well plate was then measured in the Tecan fluorescence plate reader (Ex=365±20 nm and Em=460±20 nm) after 1 hr incubation at 37° C. and addition of 100 µl/well stop solution (1 M glycine and 1 M NaOH at pH 10.5).

Intracellular and Lysosomal $Ca^{2+}$ Measurements—Intracellular cytosolic $Ca^{2+}$ concentration was measured fluorescently using a Fluo-8 dye kit (ATT Bioquest, Sunnyvale, Calif.) as described previously. Briefly, fibroblasts were cultured at 2500 cell/well in 20 µl medium in black, clear bottom 384-well plates for 24 hr at 37° C. The calcium dye mixture was added at 20 µl/well and incubated at 37° C. for 30 min following by at RT for 30 min. The plates were then placed into a fluorescence kinetic plate reader (µCell, Hamamatsu, Hamamatsu City, Japan). The basal fluorescence intensity was recorded 10 times at 1 Hz for 10 seconds and the compound was then added at 20 µl/well inside the instrument followed by additional reading at 1 Hz for 5 min. The results were normalized to the average basal fluorescence intensity in ratio and the peak response (Max.) was used for the result calculation. The lysosomal $Ca^{2+}$ induced by Gly-Phe β-napthylamide (GPN) was measured similarly as that for cytosolic $Ca^{2+}$ except 200 nM GPN was added instead of δ-T or α-T after the measurement of basal fluorescence intensity that released lysosomal $Ca^{2+}$.

Electron Microscopy—Fibroblast cells were seeded in 6-well plates at 150,000 cells/well in 5 ml medium and cultured for 1 day in the presence or absence of compounds. Cells were fixed in 2% glutaraldehyde, 0.1 M cacodylate buffer, pH 7.2 for 1 hr at room temperature and then stored at 4° C. until TEM analysis was performed. The cells were post fixed in 1% osmium tetroxide in the same buffer for 1 hour and en bloc stained with 0.5% uranyl acetate in 0.1 M acetate buffer, pH 4.2. The cells were then dehydrated in graded ethanol solutions (35%, 50%, 70%, 95% and 100%) and infiltrated overnight in epoxy resin (Poly/Bed 812, Polysciences). After adding fresh pure resin the cell plates were cured for 72 h in 55° C. After removing the polystyrene plates, suitable areas for thin sectioning were selected, cut out with a jewelry saw and glued onto empty resin stubs. About 70 nm thin sections were cut on an ultramicrotome (Leica EM UC6) and mounted on naked copper grids. The thin sections were double stained (uranyl acetate and lead citrate), examined in a Hitachi H-7650 transmission electron microscope, and images were taken using an AMT CCD camera.

In various embodiments, the invention provides a method as described above further comprising the step of administering an additional therapeutic agent.

In certain embodiments, the additional therapeutic agent is a vitamin.

In a further embodiment, the additional therapeutic agent is vitamin E.

In other embodiments, the invention provides a method as described above wherein the step of administering the cyclodextrin comprises administering the compound orally, topically, parentally, intravenously or intramuscularly.

In certain embodiments, the invention provides a method comprising the step of administering an effective amount of the compound and a pharmaceutically suitable excipient.

In certain embodiments, the invention provides a method as described above wherein the subject is a human.

In various embodiments, the step of administering the cyclodextrin comprises administering the compound to a subject such as a human in a dosage of between about 0.01 μg/kg/day and 100 mg/kg/day, either in a single dose or per day.

In another aspect, the invention provides a method of treating a lysosomal storage disorder in a subject, comprising the step of administering to the subject an effective amount of a cyclodextrin compound, or a pharmaceutically acceptable salt, ester, solvate or hydrate thereof, and an additional therapeutic agent.

In certain embodiments, the additional therapeutic agent is a vitamin.

In a further embodiment, the additional therapeutic agent is vitamin E.

In certain aspects, the invention provides a method reducing non-cholesterol lipids in a subject, the method comprising administering to the subject a cyclodextrin compound, or a pharmaceutically acceptable salt, ester, solvate or hydrate thereof; and detecting the amount of lipid reduction.

In one embodiment, the subject is identified as being in need of lipid reduction.

In another aspect, the invention provides a pharmaceutical composition comprising a therapeutically effective amount of a compound of the invention (any of the formulae presented herein), or a pharmaceutically acceptable salt, solvate or hydrate thereof, in combination with a pharmaceutically acceptable carrier or excipient.

In one embodiment, the pharmaceutical composition is in combination with a vitamin. In a further embodiment, the vitamin is vitamin E.

In another aspect, the invention provides a pharmaceutical composition comprising a cyclodextrin compound, or a pharmaceutically acceptable salt, ester, solvate or hydrate thereof, and vitamin E, together with a pharmaceutically-acceptable carrier or excipient.

In one embodiment, the cyclodextrin compound is of formula (I), or a pharmaceutically acceptable salt, ester, solvate or hydrate thereof.

In another embodiment, the cyclodextrin compound is 2-hydroxypropyl-β-cyclodextrin (2HPβCD), hydroxypropyl-β-cyclodextrin (HPβCD), methyl-β-cyclodextrin (MβCD), α-cyclodextrin, β-cyclodextrin, or γ-cyclodextrin, or a pharmaceutically acceptable salt, ester, solvate or hydrate thereof.

In another aspect, the invention provides a method of treating a subject suffering from a lysosomal storage disorder, comprising the use of the pharmaceutical composition as described above, in combination with another agent.

In other aspects, the invention provides a kit comprising an effective amount of a cyclodextrin compound, or a pharmaceutically acceptable salt, ester, solvate or hydrate thereof, in unit dosage form, together with instructions for administering the compound to a subject suffering from a lysosomal storage disorder.

In one embodiment, the cyclodextrin compound is of formula (I), or a pharmaceutically acceptable salt, ester, solvate or hydrate thereof.

In another embodiment, the cyclodextrin compound is 2-hydroxypropyl-β-cyclodextrin (2HPβCD), hydroxypropyl-β-cyclodextrin (HPβCD), methyl-β-cyclodextrin (MβCD), α-cyclodextrin, p62-cyclodextrin, or γ-cyclodextrin, or a pharmaceutically acceptable salt, ester, solvate or hydrate thereof.

In another embodiment, the kit further comprises vitamin E.

In another embodiment, the invention provides a method as described above further comprising the step of synthesizing or obtaining the cyclodextrin compounds. Yet another embodiment of the present invention is a process of making any of the compounds delineated herein employing any of the synthetic means delineated herein, or using methods known to one of ordinary skill in the art.

In certain embodiments, cyclodextrins including α-, β- and γ-cyclodextrins increased intracellular Ca2+ and lysosomal exocytosis in both wild type and cells with LSDs (Wolman disease).

In various embodiments, cyclodextrins reduced enlarged lysosomes in six cell lines with LSDs.

In another embodiment, cyclodextrins reduced ultrastructural pathologic changes in cells with Wolman diseases and other cells.

In certain embodiments, cyclodextrins in combination with tocopherol synergistically/additively reduced cholesterol accumulation in cells of NPC and Wolman diseases.

An inhibitory amount or dose of the compounds of the present invention may range from about 0.1 mg/kg to about 500 mg/kg, alternatively from about 1 to about 50 mg/kg. Inhibitory amounts or doses will also vary depending on route of administration as well as the possibility of co-usage with other agents.

The term "inhibitory amount" of a compound of the present invention means a sufficient amount to decrease the disorder in a biological sample or a subject. It is understood that when said inhibitory amount of a compound of the present invention is administered to a subject it will be at a reasonable benefit/risk ratio applicable to any medical treatment as determined by a physician. The term "biological samples(s),'' as used herein, means a substance of biological origin, which may be intended for administration to a subject. Examples of biological samples include, but are not limited to, plasma, blood and components thereof such as plasma, platelets, subpopulations of blood cells and the like; organs such as kidney, liver, heart, lung, and the like; sperm and ova; bone marrow and components thereof; or stem cells.

As referred to herein, the phrase "in combination with", or "or conjunction with" when referring to administration of a cyclodextrin compound and an additional therapeutic agent (distinct from the cyclodextrin compound) such as a vitamin E compound is intended to refer to all forms of administration that provide the cyclodextrin and additional therapeutic single unitary formulation) or sequentially in any order. For instance, in a suitable aspect, for sequential administration, the cyclodextrin compound and the additional therapeutic agent may be formulation separately and administered within about 0.25, 0.5, 1, 2, 5, 10, 15, 20, 30, 40, 50, or 60 minutes or more of each other. For sequential administration, preferably the cyclodextrin compound and the additional therapeutic agent may be formulated separately and administered within about 30, 20, 10 or 5 minutes or less of each other.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgement. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples the roof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses. For instance a compound of the present invention can be administered to a patient twice a day with a total daily dose of 4000, 4200, 4400, 4600, 4800 or 5000 mg.

A preferred single use of cyclodextrin for mammals including humans is from 0.1 mg/Kg to 8 mg/Kg, more preferably 0.5 mg/kG or 1.0 mg/Kg to 2 mg/Kg, 3 mg/Kg, 4 mg/Kg, 5 mg/Kg, 6 mg/Kg, 7 mg/Kg or 84 mg/Kg. One specific preferred single use of cyclodextrin for mammals including humans is 3 mg/Kg.

In combination therapy of a cyclodextrin compound administered together or otherwise in conjunction with a vitamin E compound such as delta-tocopherol, a preferred single dose for a mammal including a human may be from 0.05 to 1 mg/kg for each of the cyclodextrin compound and vitamin E compound (such as delta-tocopherol), more preferably 0.1 mg/Kg to 0.5 mg/Kg, 0.6 mg/Kg or 0.7 mg/Kg for each of a cyclodextrin compound and vitamin E compound such as delta-tocopherol, still more preferably 0.1 mg/Kg to 0.3 mg/Kg or 0.4 mg/Kg for each of a cyclodextrin compound and vitamin E compound such as delta-tocopherol.

In embodiments of the present invention, treatment of a lysosomal storage disorder with a combination of a cyclodextrin compound and vitamin E compound (such as delta-tocopherol) can allow for use of a lower dosage of the cyclodextrin compound to achieve a therapeutic effect than when the cyclodextrin compound is used alone. In certain aspects, the amount of the cyclodextrin compound administered is at least 5%, at least 10%, at least 15%, at least 20%, at least 25%, at least 30%, at least 35%, at least 40%, at least 50%, at least 55%, at least 60%, at least 65%, at least 70%, at least 75%, at least 80%, at least 85%, or at least 90%, less than an amount of the cyclodextrin compound necessary to achieve a therapeutic effect if administered without the vitamin E compound.

Biological Data

FIG. 1. (amplex red) Skin fibroblasts derived from NPC1 patients demonstrate profound and reproducible cholesterol accumulation in late endosomes and lysosomes and, therefore, provide a robust cellular model of NPC1 disease. Using a phenotypic screen with a biochemical assay (Amplex Red) to measure unesterified cholesterol: Delta-Tocopherol)"δ-T"; or "Delta-T") δ-T was identified as a lead compound that dramatically reduces cellular cholesterol accumulation in a concentration dependent manner. We further evaluated effect of cyclodextrins alone and in combination with delta Tocopherol in other lysosomal storage disorders and we found that alpha-CD, beta-CD, and gamma-CD can reduce cholesterol accumulation, and MBCD was most potent.

Figure 2:
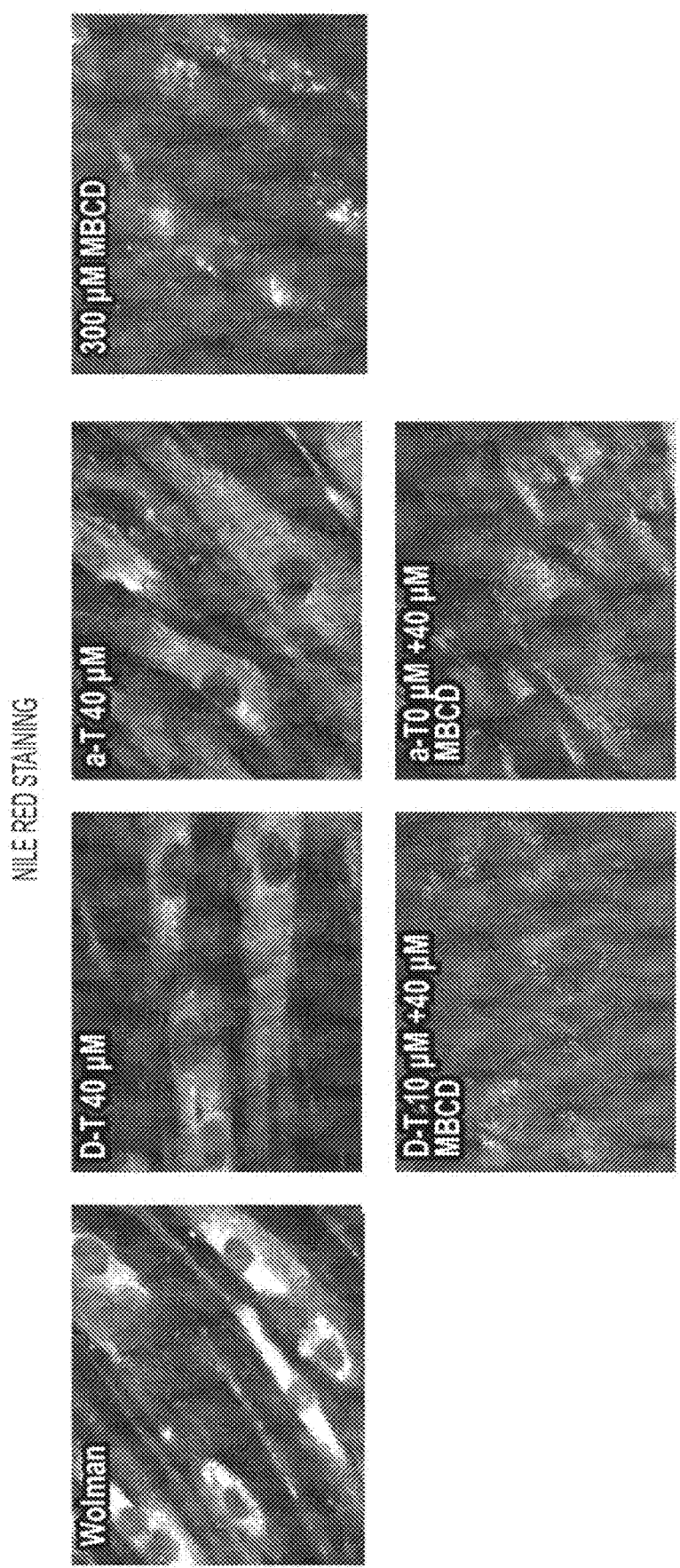
FIG. 2 is a set of photographs showing Nile Red staining of Wolman fibroblasts treated with δ-tocopherol (D-T), α-tocopherol (a-T), methyl-β-cyclodextrin, and combinations of δ-tocopherol (D-T) and methyl-β-cyclodextrin (MBCD), and α-tocopherol and methyl-β-cyclodextrin.

FIG. 2. (Nile Red) Cells were cultured in the presence of delta tocopherol, alpha tocopherol and MBCD plus in combination for 3 days and then stained for neutral lipid with Nile red. Delta Tocopherol and MBCD treatment reduces accumulation of neutral lipids and it is more pronounced when used in combination. Alpha Tocopherol was not as potent.

Figure 3:
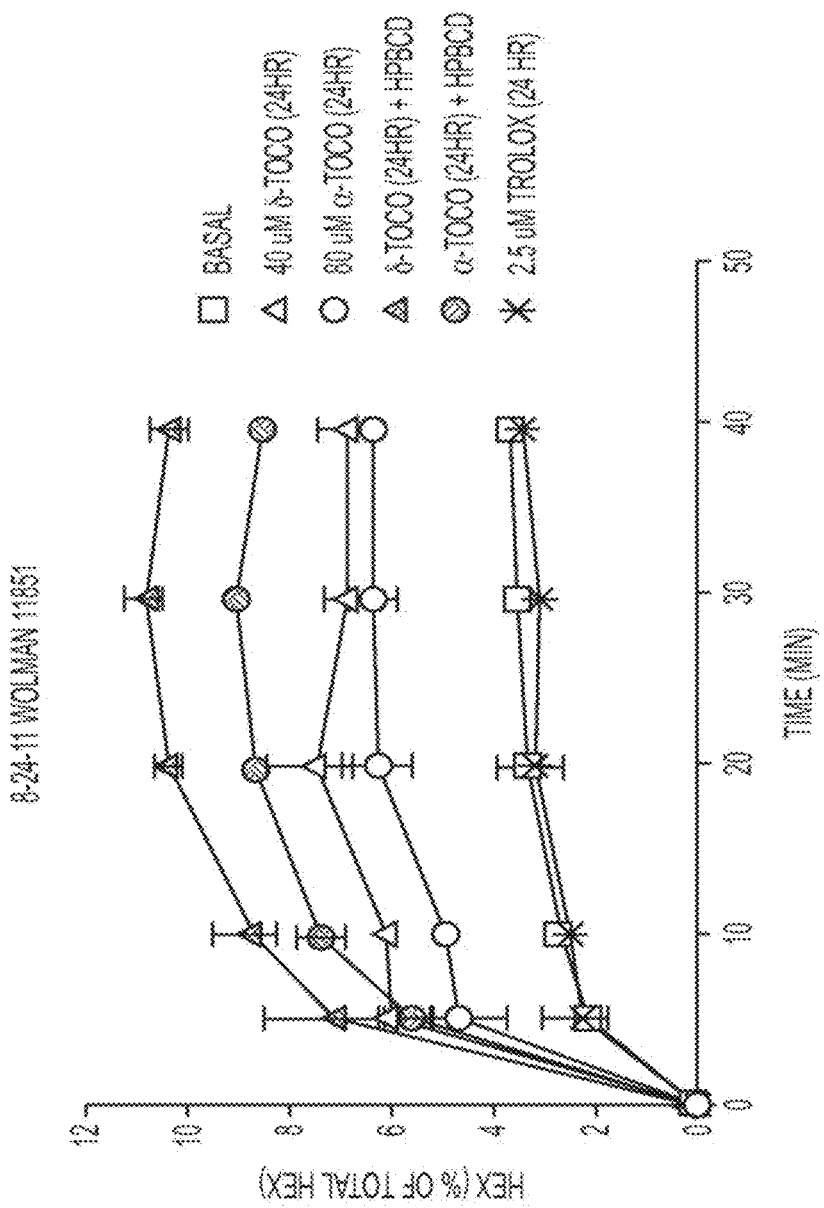
FIG. 3 is a set of graphs showing exocytosis levels in Wolman fibroblasts as measured by HEXB secretion.
Figure 3:
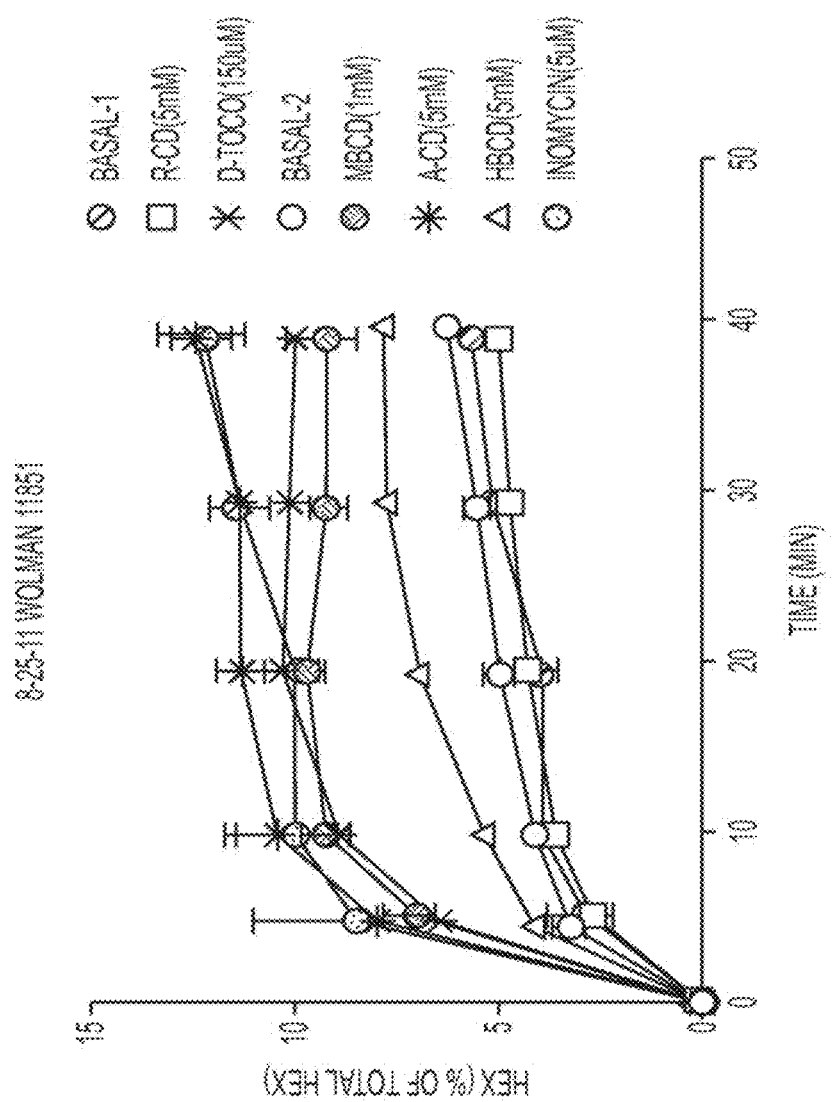

FIG. 3. (Hex assay) Delta-T stimulates lysosomal exocytosis in Wolman fibroblasts. 2-hydroxypropyl-beta-cyclodextrin has been reported to promote a calcium-dependent lysosomal exocytosis, which offers a potential mechanism for its cholesterol-reducing effect in LSD fibroblast. We measured lysosomal exocytosis in delta-T-treated Wolman fibroblasts by determining the activity of beta-hexosaminidase (HEXB), a lysosomal enzyme, in the extracellular medium. We found that HEXB activity increased in culture medium after 40 μM δ-Tocopherol treatment for 24 hours compared with the vehicle treated cells. These results demonstrate that the pharmacological effect of delta-T may be mediated by the increase of cytosolic $Ca^{2+}$ and enhancement of lysosomal exocytosis.

Figure 4A:
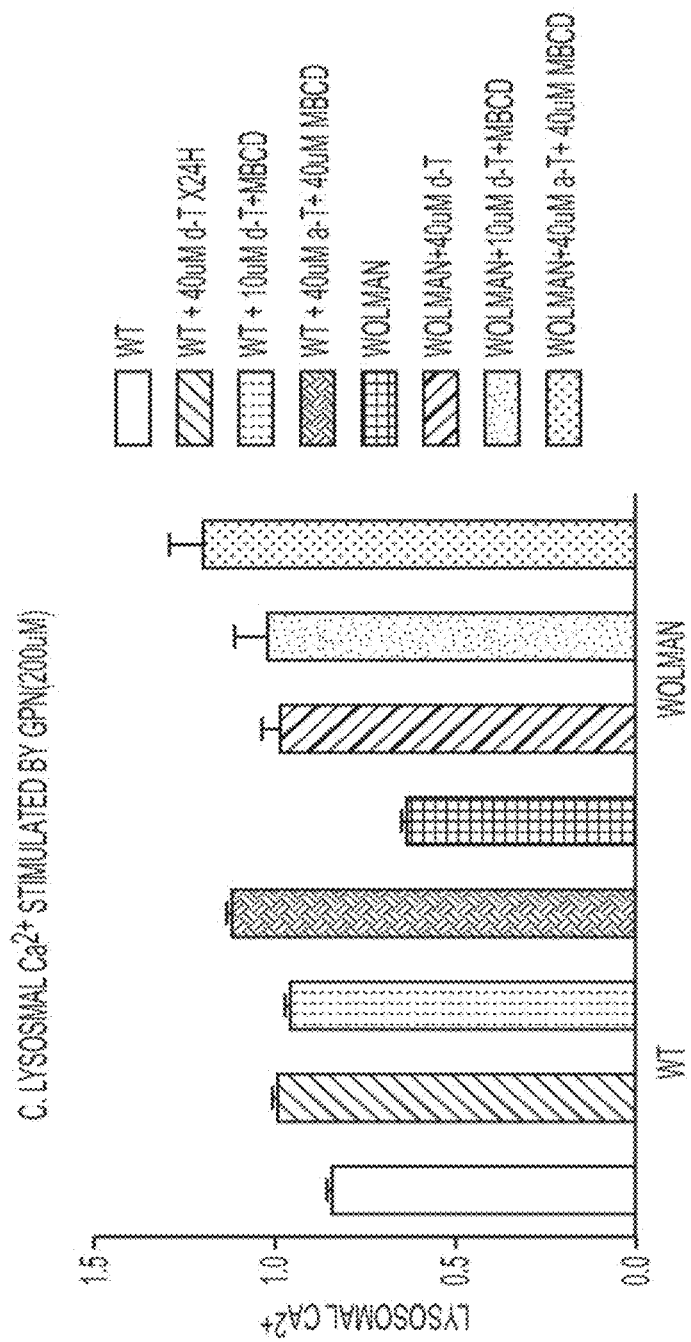
FIG. 4 is a set of graphs showing lysosomal calcium efflux in wild-type fibroblasts and lysosomal storage disease fibroblasts in the presence and absence of δ-tocopherol, α-tocopherol, methyl-β-cyclodextrin, and combinations of δ-tocopherol and methyl-β-cyclodextrin, and α-tocopherol and methyl-β-cyclodextrin.
Figure 4:
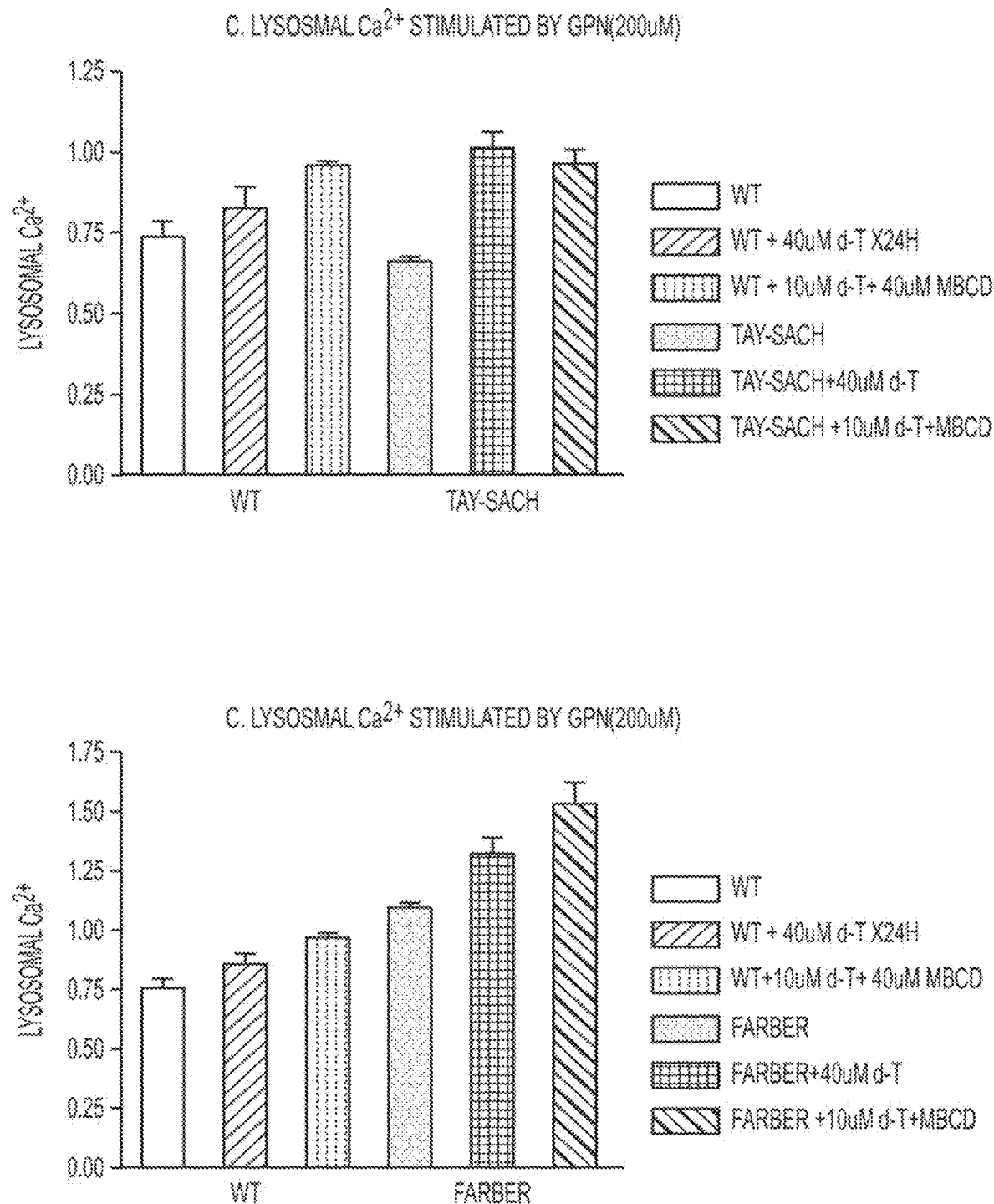
Figure 4:
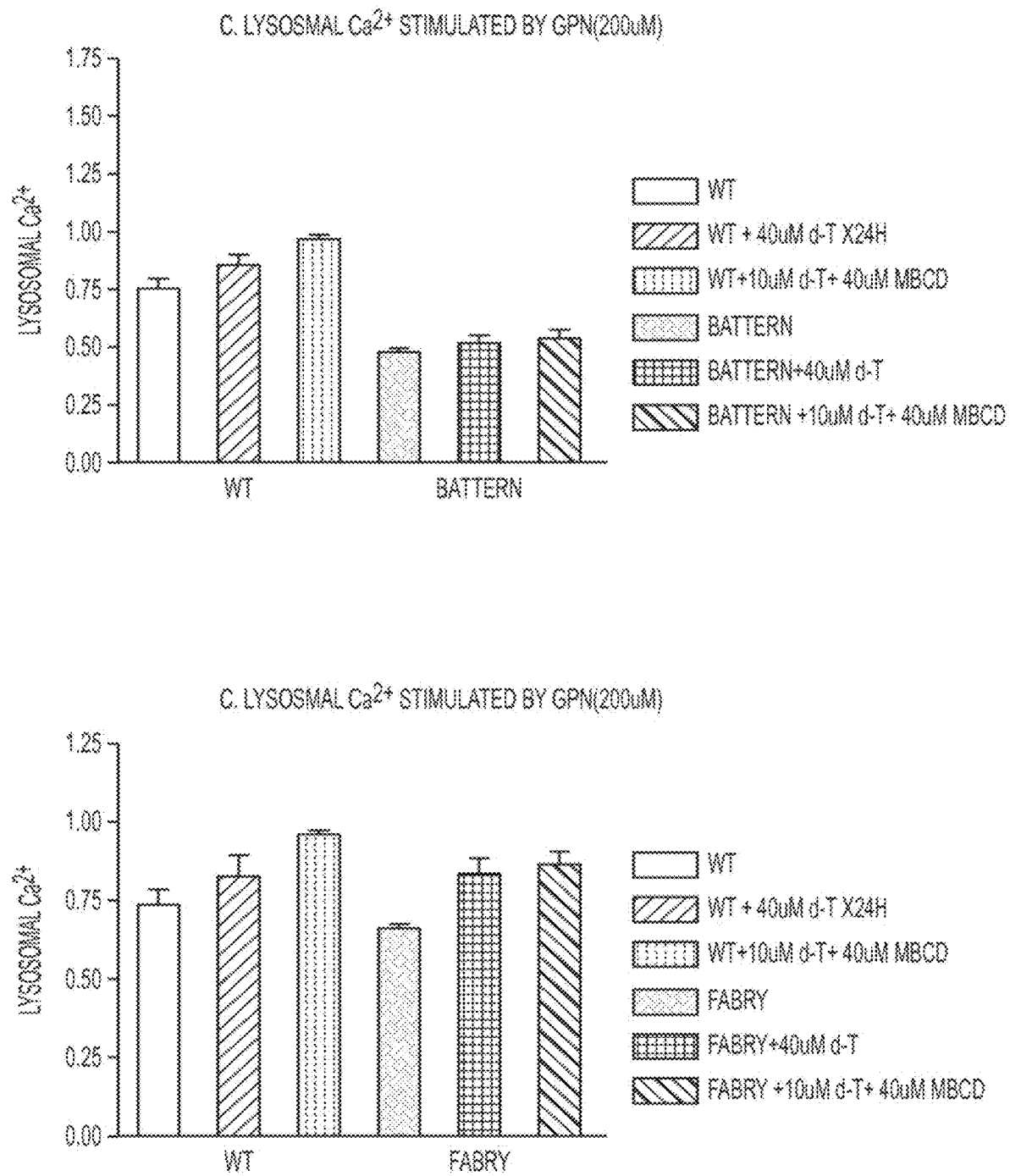
Figure 5A:
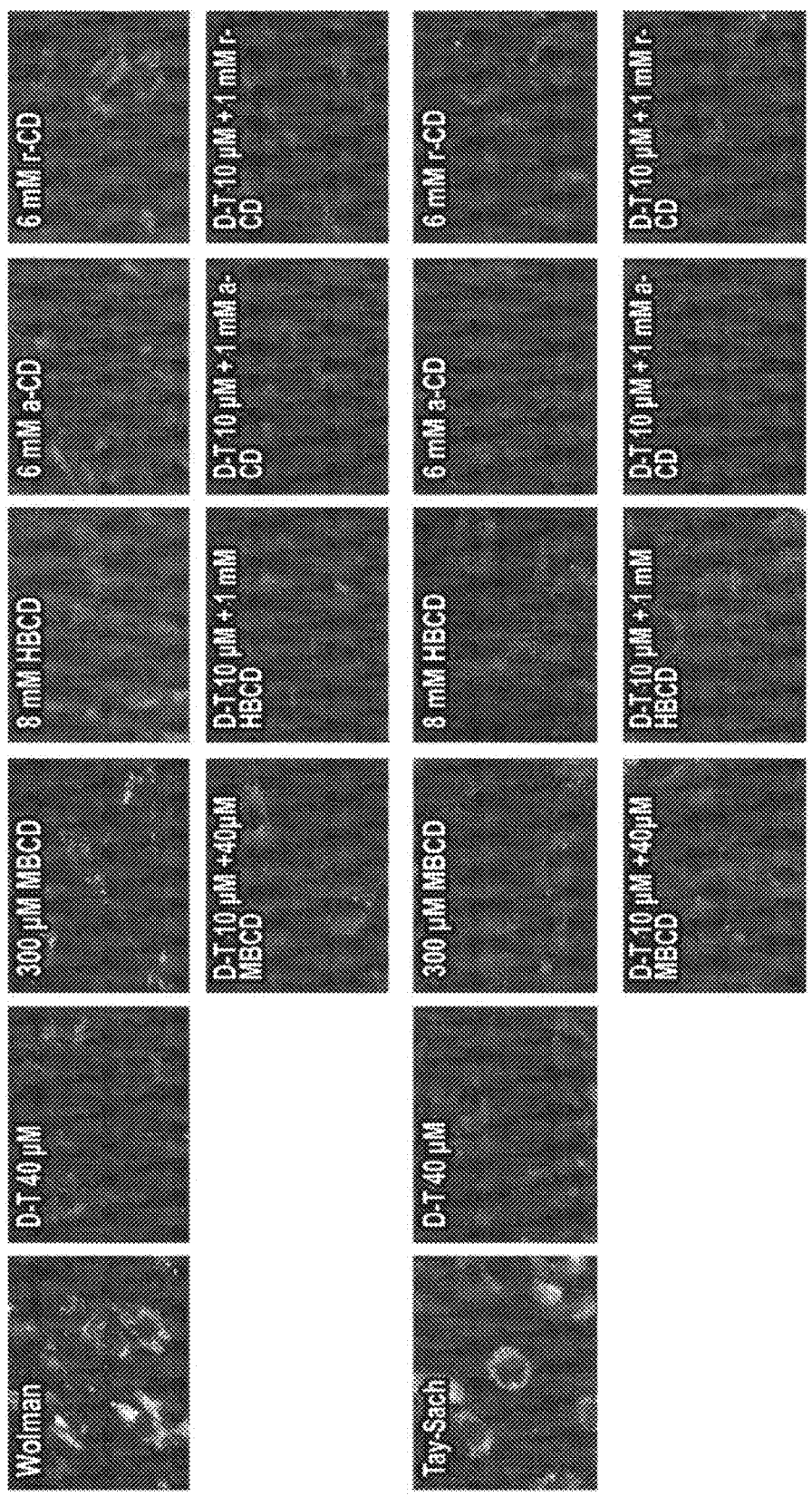
FIGS. 5A-5D are sets of photographs showing the effect of various forms of Cyclodextrins (a-CD, r-CD), δ-Tocopherol (D-T), and combinations in seven disease and wild-type fibroblast cell lines as measured using the Lysotracker assay. Highly branched cyclodextrin (HBCD), also known as Kleptose.
Figure 5B:
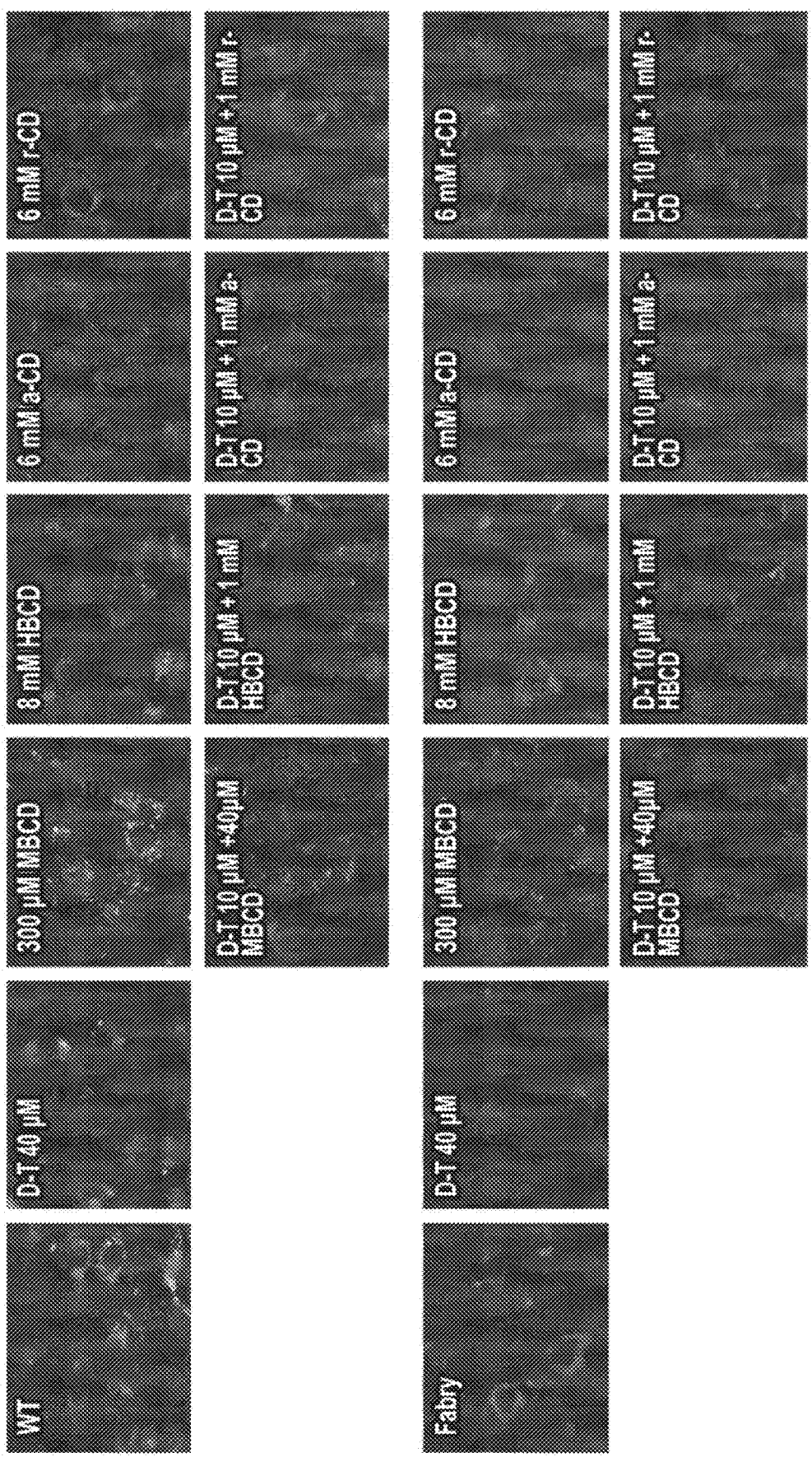
Figure 5C:
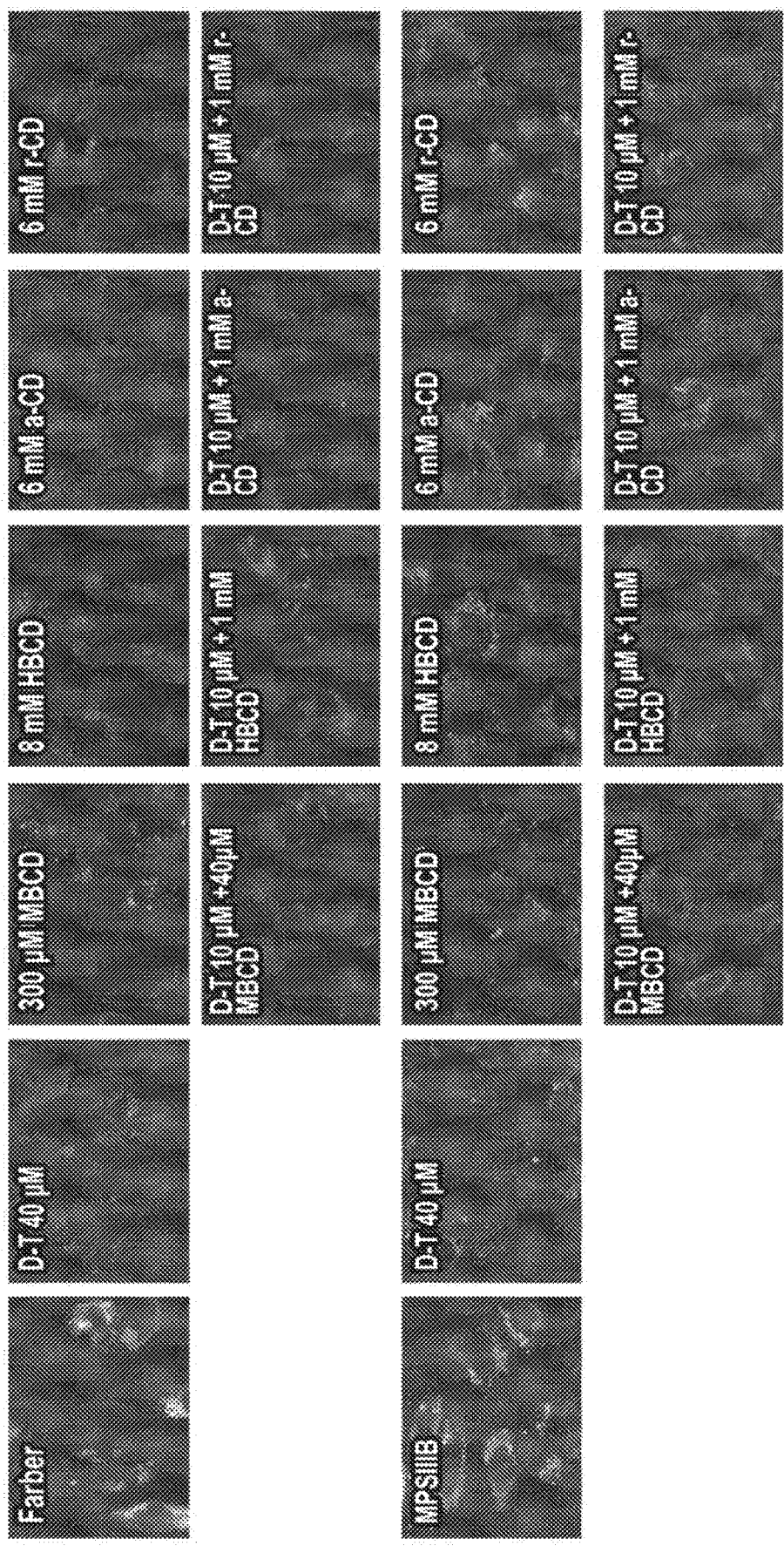
Figure 5D:
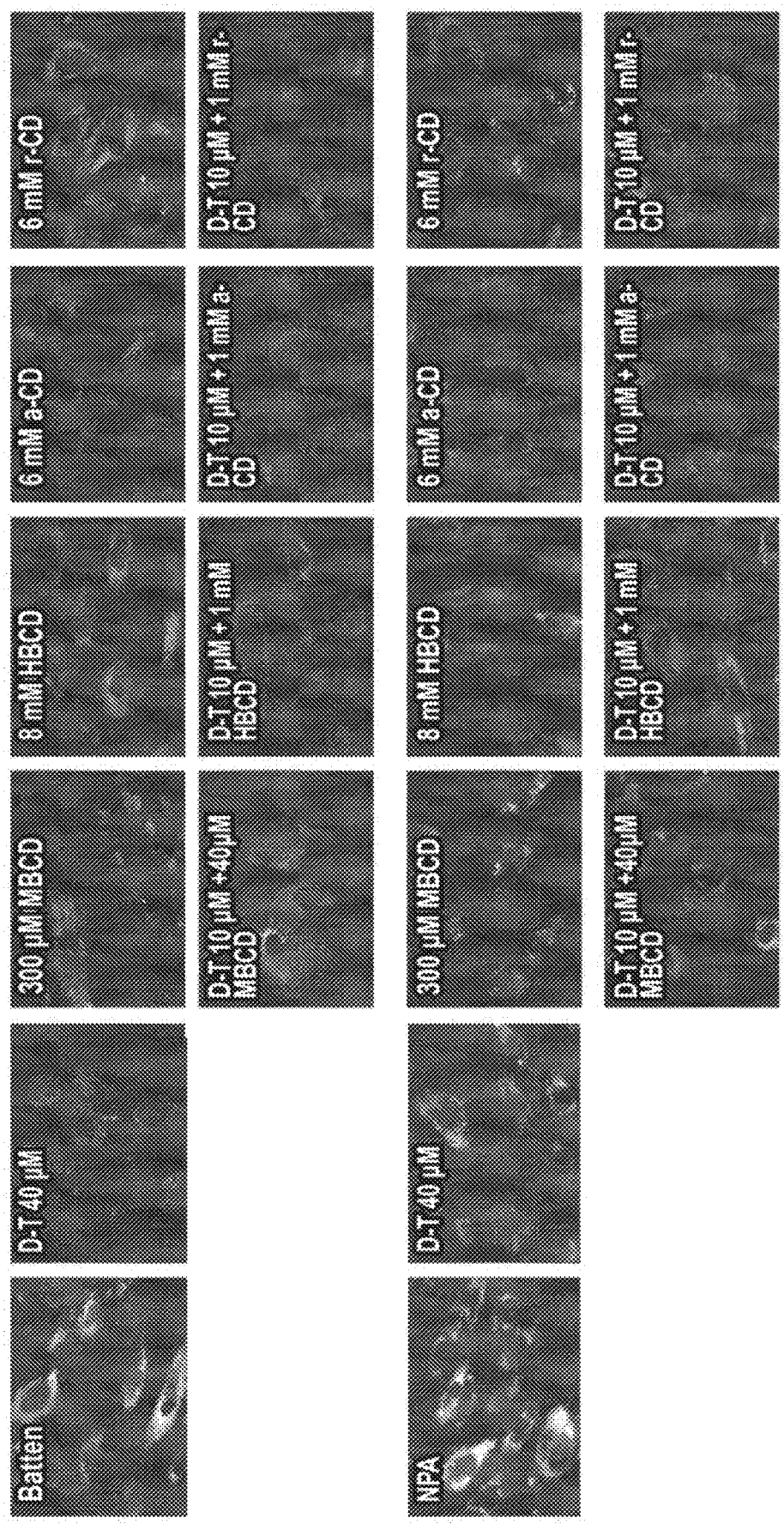

FIG. 4. (calcium assay) Delta-T increases intracellular $Ca^{2+}$ concentration and ameliorates lysosomal calcium deficiency in NPC1 cells—Increase in the concentration of intracellular $Ca^{2+}$, an important second messenger, triggers a variety of cellular responses including lysosomal exocytosis. In NPC1 fibroblasts there is a dysregulation of calcium homeostasis, as evidenced by lysosomal $Ca^{2+}$ deficiency. Treatments that compensate for loss of lysosomal $Ca^{2+}$ (e.g., curcumin) have been reported to reduce cholesterol storage in NPC1 cells. To explore whether delta-T may similarly exert its effects through changes in intracellular $Ca^{2++}$, we measured cytosolic calcium levels in both NPC1 and Wolman cells following the treatment with δ-T. We found that δ-T stimulated a transient increase of cytosolic $Ca^{2+}$ in both NPC1 and Wolman fibroblasts, as well as in control fibroblasts. In addition, the intracellular $Ca^{2+}$ response to delta-T was independent of extracellular $Ca^{2+}$ concentration, indicating that $Ca^{2+}$ was released from intracellular storage sites such as the ER in response to δ-T. We further studied the effect of delta-T on lysosomal $Ca^{2+}$ released by Gly-Phe β-naphthylamide (GPN) in NPC1 fibroblasts. Consistent with an earlier report, lysosomal $Ca^{2+}$ was reduced in NPC1 cells compared with that in control cells. Treatment of NPC1 fibroblasts with 40 μM delta-T for 24 hours significantly increased lysosomal $Ca^{2+}$.

FIG. 5. Based on the data for both NPC1 and Wolman cells, we hypothesized that the pharmacological effect of delta-T on the intracellular $Ca^{2+}$ and lysosomal exocytosis is a general mechanism for elimination of lysosomal storage. To test this hypothesis we measured the ability of delta-T to decrease acidic/lysosomal compartment size as determined by LysoTracker staining in fibroblasts derived from patients with six other diseases. Lysosomal storage occurs in these fibroblasts consists of ceroid/lipofuscin in Batten (CLN2), globotriaosylceramide in Fabry, ceramide in Farber, sphingomyelin in NPA, partially degraded heparan sulfate in Sanfilippo type B, and GM2 ganglioside in Tay-Sachs (Table S1). Whereas untreated fibroblasts showed increased LysoTracker staining, indicating the enlarged lysosomes treatment with 40 μM delta-T significantly reduced the LysoTracker staining in all six fibroblast cell lines studied. Thus, the amelioration of lysosomal pathology by delta-T, initially demonstrated in NPC1 and Wolman cells, can be generalized to other lysosomal storage diseases.

The mixed lipid storage phenotype results in a marked enlargement of lysosomes in the NPC1 and Wolman fibroblasts. Therefore, we next determined whether the enlarged lysosomes in these cells could be reduced by the treatment with δ-T. LysoTracker, a probe which stains the intracellular acidic compartment, has been used to visualize the enlarged endolysosomal compartment in NPC1 cells. We found increased LysoTracker staining in both NPC1 and Wolman fibroblasts, as expected. Treatment with either 40 μM delta-T or 300 μM MBCD significantly reduced LysoTracker staining in both types of fibroblasts.

Figure 6:
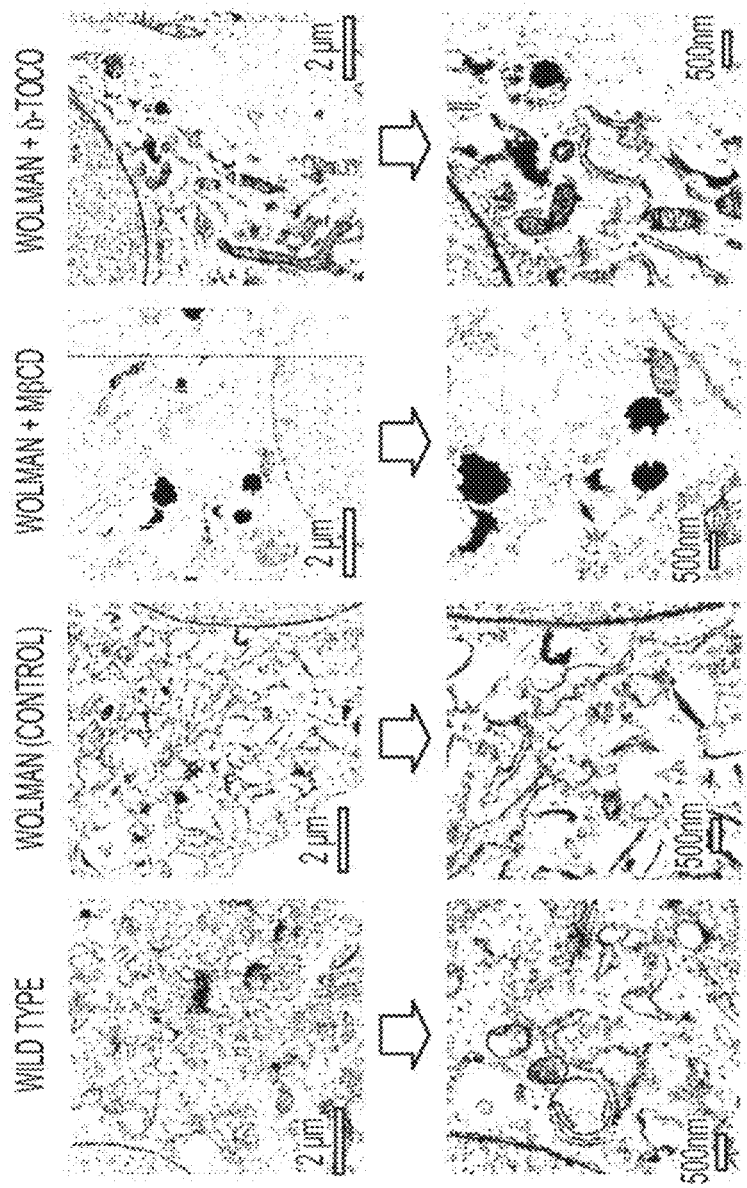
FIG. 6 is a set of photographs showing that cyclodextrin alleviates pathological ultrastructural changes in Wolman disease cells, methyl-β cyclodextrin (MBCD), δ-tocopherol (δ-toco).

FIG. 6. Both NPC1 and Wolman fibroblasts have a distinct ultrastructural phenotype that is evident by electron microscopy. The reduction of acidic cellular compartments by delta-T treatment is consistent with decreased intracellular storage that was confirmed by alleviation of the ultrastructural pathology.

The electron microscopic images exhibited enlarged lysosomes full of lamellated membranes and dense osmiophilic material in NPC1 cells and lipid droplet-like and cleft-like lysosomes in Wolman cells. Treatment with 40 μM delta-T significantly reduced the characteristic storage materials in lysosomes of both cell types. Together, these finding demonstrate that the delta-T-mediated cholesterol reduction is associated with alleviation of the disease phenotypes in NPC1 and Wolman cells.

We have found that alpha-CD, beta-CD, and gamma-Cd can reduce cholesterol accumulation in NPC cells. We also found that these CDs increased intracellular Ca2+ and enhanced exocytosis. The ranking order of cholesterol reduction effect is MBCD>alpha-CD>gamma-CD. In addition we found that the CD treatment reduced the pathological changes in the ultrastructure of NPC cells using the electron microscopy analysis. We also found that CDs reduced enlarged lysosomes in the primary fibroblasts of Wolman disease another lysosomal storage disease that exhibits cholesterol ester accumulation due to the malfunction of acid lipase in lysosome. The electron microscopy data indicated that the CD effect is more significant than that of delta-tocopherol in the Wolman cells.

We also found the synergy between CD and delta-tocopherol on the NPC cells and other 6 lysosomal storage disease cells including Wolman, Niemann Pick Type A, Farber, Tay-Sachs, MSIIIB and CLN2 (Batten) diseases. The fluorescence tagged CD study indicated that CD enters cell and comes out of cell quickly, indicating via exocytosis. We also have the data demonstrate that alpha-CD, beta-CD and gamma-CD enhance exocytosis.

Definitions

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$-$C_y$," where x is the minimum and y is the maximum number of carbon atoms in the substituent. Likewise, a $C_x$ chain means a hydrocarbyl chain containing x carbon atoms.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein at least one hydrogen radical is replaced with a halogen radical.

If a linking element in a depicted structure is "absent" or "a bond", then the left element in the depicted structure is directly linked to the right element in the depicted structure. For example, if a chemical structure is depicted as X-(L)$_n$—Y wherein L is absent or n is 0, then the chemical structure is X—Y.

The term "alkyl" as used herein, refers to a saturated, straight- or branched-chain hydrocarbon radical. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched chain hydrocarbon radical containing one or more double bonds. For example, "$C_2$-$C_8$ alkenyl" contains from two to eight carbon atoms. Alkenyl groups include, but are not limited to, for example, ethenyl, propenyl, butenyl, 1-methyl-2-buten-1 yl, heptenyl, octenyl and the like.

The term "alkynyl" as used herein, denotes a straight- or branched-chain hydrocarbon radical containing one or more triple bonds. For example, "$C_2$-$C_8$ alkynyl" contains from two to eight carbon atoms. Representative alkynyl groups include, but are not limited to, for example, ethynyl, 1-propynyl, 1-butynyl, heptynyl, octynyl and the like.

The term "cycloalkyl" denotes a monovalent group derived from a monocyclic or polycyclic saturated carbocyclic ring compound. Examples of cycloalkyl include, but not limited to, cyclopropyl, cyclobutyl, cyclopentyl, cyclohexyl, bicyclo [2.2.1] heptyl, and bicyclo [2.2.2] octyl and the like. The terms "carbocycle" or "carbocyclic" or "carbocyclyl" refer to a saturated (e.g., "cycloalkyl"), partially saturated (e.g., "cycloalkenyl" or "cycloalkynyl") or completely unsaturated (e.g., "aryl") ring system containing zero heteroatom ring atom. A carbocyclyl may be, without limitation, a single ring, or two or more fused rings, or bridged or spiro rings. A carbocyclyl may contain, for example from 3 to 10 ring members (i.e., $C_3$-$C_{10}$carbocyclyl, such as $C_3$-$C_{10}$cycloalkyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl and the like. A carbocyclyl group can be attached to the parent molecular moiety through any substitutable carbon atom of the group.

The term "aryl" refers to an aromatic carbocyclyl containing from 6 to 14 carbon ring atoms. Non-limiting examples of aryls include phenyl, naphthalenyl, anthracenyl, and indenyl and the like. An aryl group can be connected to the parent molecular moiety through any substitutable carbon atom of the group.

The term "heteroaryl" means an aromatic heterocyclyl typically containing from 5 to 18 ring atoms, wherein at least one ring atom is a heteroatom. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,3-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heterocycloalkyl" refers to a non-aromatic 3-, 4-, 5-, 6- or 7-membered ring or a bi- or tri-cyclic group fused system, where at least one of the ring atoms is a heteroatom, and where (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above rings may be fused to a benzene ring. Representative heterocycloalkyl groups include, but are limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

The terms "heterocyclic" or "heterocycle" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atoms in the group, provided that a stable molecule results. A heterocyclyl may be, without limitation, a single ring. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituent including, but not limited to:

-alkyl, -alkenyl, -alkynyl, -aryl, -arylalkyl, -heteroaryl, -heteroarylalkyl, -heterocycloalkyl, -cycloalkyl, -carbocyclic, -heterocyclic, —F, —Cl, —Br, —I, —OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —(O)-cycloalkyl, —C(O)-aryl, —C(O)-heteroaryl, —C(O)-heterocycloalkyl, —$CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NCH(O)-aryl, —NHC(O)-heteroaryl, —NHC(O)-heterocycloalkyl, —$NHCO_2$-alkyl, —$NHCO_2$-alkenyl, —$NHCO_2$-alkynyl, —$NHCO_2$-cycloalkyl, —$NHCO_2$-aryl, —$NHCO_2$-heteroaryl, —$NHCO_2$-heterocycloalkyl, —NHC(O)$NH_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, NHC(S)NH$_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)NH$_2$, NHC(NH)-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —(O)-cycloalkyl, —S(O)-aryl, —S(O)-heteroaryl, —S(O)-heterocycloalkyl —SO$_2$NH$_2$, —SO$_2$NH-alkyl, —SO$_2$NH-alkenyl, —SO$_2$NH-alkynyl, —SO$_2$NH-cycloalkyl, —SO$_2$NH-aryl, —SO$_2$NH-heteroaryl, —SO$_2$NH-heterocycloalkyl, —NHSO$_2$-alkyl, —NHSO$_2$-alkenyl, —NHSO$_2$-alkynyl, —NHSO$_2$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —-heteroaryl, —S-heterocycloalkyl, or methylthiomethyl.

It is understood that the aryls, heteroaryls, carbocycles, heterocycles, alkyls, and the like can be further substituted.

The terms "halo" and "halogen," as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

The term "non-cholesterol lipid" is meant to refer to any lipid that is not cholesterol, for example a macromolecule. Exemplary non-cholesterol lipids include, but are not limited to, lipopigments, globotriaosylceramide, ceramide, sphingomyelin, heparan sulfate, partially degraded heparan sulfate, GM2 ganglioside, triglycerides, and cholesterol esters, and derivatives thereof. A "non-cholesterol dominant lipid" is meant to refer to any lipid that is not cholesterol, that is present in an amount greater than cholesterol making it the non-cholesterol dominant lipid.

The term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

The term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups are known in the are described generally in T. H. Greene and P. G. M. Wuts, Protective Groups in Organic Synthesis, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimesthylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsily, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "alkylamino" refers to a group having the structure —N(R$_a$R$_b$), where R$_a$ and R$_b$ are independent H or alkyl.

As used herein, the term "pharmaceutically acceptable salt" refers to those salts of the compounds formed by the process of the present invention which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionante, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for us in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et. al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis in Drug And Prodrug Metabolism: Chemistry, Biochemistry And Enzymology," John Wiley and Sons, Ltd. (2002).

This invention also encompasses pharmaceutical compositions containing pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters.

Free hydroxy groups may be derivatized using groups including but not limited to hemisuccinates, phosphate esters, dimethylaminoacetates, and phosphoryloxymethyloxy carbonyls, as outlined in Advance Drug Delivery Reviews, 1996, 19, 1 15. Carbamate prodrugs of hydroxy and amino groups are also included as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, "solvate" refers to the physical association of a compound of the invention with one or more solvent molecule, whether organic or inorganic. This physical association often includes hydrogen bonding. In certain instances, the solvate is capable of isolation, for example, when one or more solvate molecules are incorporated in the crystal lattice of the crystalline solid.

Combination of substituents and variable envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formylation auxiliary of any type. The pharmaceutical compositions of this invention can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnui, corn, germ, olive, castor, and sesame oils), mono- or diglycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizing agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed including synthetic mono- or diglycerides. In addition, fatty acids such as oleic acid are used in the preparation of injectables.

In certain preferred embodiments, the compositions of the present invention are administered intracranially, for instance injected into the brain, such as by direct injection into the brain. Direct injection may be performed by intraventricular and intracerebral routes. Injection of the compositions into the brain can also be performed using a device for administration. Because cyclodextrin and delta-tocopherol may pose a challenge with brain penetration and quick drug metabolism, direct administration of the drugs into the central nervous system may be achieved by using epidural (injection or infusion into the epidural space), intracerebral (into the cerebrum), intracerebroventricular (into the cerebral ventricles), or intrathecal (into the spinal canal) injection. Pathan et al. (Recent Patents on Drug Delivery & Formulation 2009, 3, 71-89), incorporated by reference in its entirety herein, describes some method of administration of a composition to the brain.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above.

The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Preferably, a compound of the invention is formulated in a solid dispersion, where the compound can be molecularly dispersed in a matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt extrusion, spray drying, or solvent evaporation.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonities, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds described herein contain one or more asymmetric centers and thus give rise to enantiomers, diastereomers, and other stereoisomeric forms that may be defined, in terms of absolute sterochemistry, as (R)- or (S)-, or as (D)- or (L)-for amino acids. The present invention is meant to include all such possible isomers, as well as their racemic and optically pure forms. Optical isomers may be prepared from their respective optically active precursors aby the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can bb separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. The following examples can be prepared according to the schemes as described above, or according to the synthetic steps as described below. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The chemical structures herein contain certain —NH—, —NH$_2$ (amino) and —OH (hydroxyl) groups where the corresponding hydrogen atom(s) may not explicitly appear, however they are to be read as —NH—, —NH$_2$ or —OH as the case may be.

Example 1: δ-Tocopherol and Cyclodextrin Treatment Reduces Lipid Accumulation in Lysosomes of Lysosome Storage Disorder Cells The effect of methyl-β-cyclodextrin on lipid accumulation in fibroblast lines derived from patients with Wolman disease was investigated. Wolman fibroblasts were treated with δ-tocopherol, α-tocopherol, methyl-β-cyclodextrin, or combinations of δ-tocopherol and methyl-β-cyclodextrin or α-tocopherol and methyl-β-cyclodextrin. Total cholesterol and free cholesterol were then measured using the Amplex-Red Cholesterol Oxidase assay (Invitrogen) according to the manufacturer's instructions. As shown in FIGS. 1A-1C (Total cholesterol) and in FIGS. 1D-1F (Free cholesterol), treatment with δ-tocopherol, methyl-β-cyclodextrin, or combinations of δ-tocopherol and methyl-β-cyclodextrin or α-tocopherol and methyl-β-cyclodextrin caused a significant reduction in total cholesterol and free cholesterol in Wolman fibroblasts. To further characterize the effect of treatment on lipid accumulation, treated fibroblasts were evaluated using a Nile Red assay to measure neutral lipid accumulation. In brief, cells treated with various drugs were stained with Nile Red which selectively labels lipid accumulations within cells. The Nile Red staining was visualized by fluorescent microscopy. As shown in FIG. 2, untreated Wolman fibroblasts show cytoplasmic droplets of neutral lipid accumulation. These neutral lipid accumulations were significantly reduced upon treatment with δ-tocopherol or methyl-β-cyclodextrin. Interesting, α-tocopherol treatment failed to show any effect on neutral lipid accumulation.

The effects of δ-tocopherol, α-tocopherol, methyl-β-cyclodextrin, or combinations of δ-tocopherol and methyl-β-cyclodextrin or α-tocopherol and methyl-β-cyclodextrin treatment on lysosomal exocytosis were determined using the HEXB assay. In brief, the level of lysosomal exocytosis was determined by measuring the level of the lysosomal enzyme HEXB secreted into the culture medium following treatment with drug. As shown in FIG. 3, treatment with α-tocopherol, methyl-β-cyclodextrin, or combinations of δ-tocopherol and methyl-β-cyclodextrin or α-tocopherol and methyl-β-cyclodextrin resulted in significant increases in lysosomal exocytosis as determined by HEXB secretions. The highest levels of exocytosis were seen in Wolman fibroblasts treated with the combination of δ-tocopherol and methyl-β-cyclodextrin.

To further characterize the effects of cyclodextrin on lysosome function in fibroblast lines derived from patients with lysosomal storage diseases (Wolman, Tay-Sach, Farber, Battern, and Fabry), the effect of cycoldextrin treatment on lysosomal Ca$^{2+}$ release was determined. Both wild-type and lysosomal storage disease fibroblasts were treated with combinations of δ-tocopherol and methyl-β-cyclodextrin or α-tocopherol and methyl-β-cyclodextrin and the levels of lysosomal Ca$^{2+}$ release stimulated by 200 nM Gly-Phe β-naphthylamide (GPN) was measured. As shown in FIG. 4, untreated lysosomal storage disease fibroblasts displayed reduced Ca$^{2+}$ release compared to untreated wild-type fibroblasts. However, treatment of Wolman fibroblasts, Tay-Sach fibroblasts, Farber fibroblasts, Battern fibroblasts, and Fabry fibroblasts with combination of δ-tocopherol and methyl-β-cyclodextrin or α-tocopherol and methyl-β-cyclodextrin restored lysosomal Ca$^{2+}$ release to those levels seen in wild-type fibroblasts.

The effect of various cyclodextrins, δ-tocopherol, and combinations of cyclodextrins and δ-tocopherol on lipid accumulation and lysosome size in wild-type and lysosomal storage disease fibroblasts (Wolman, Tay-Sach, Fabry, Farber, and MPSIIIB fibroblasts) was determined using Lysotracker assay. In brief, cells were treated with various combinations and concentrations of drugs followed by staining with the Lyso tracker dye which is a basophilic fluorescent probe that accumulates in acidic compartments, i.e. lysosomes, within the cell. As shown in FIGS. 5A-5D, Lysotracker staining revealed enlarged lysosomes in Wolman, Tay-Sach, Fabry, Farber, and MPSIIIB fibroblasts compared to wild-type cells. Treatment with δ-tocopherol or methyl-β-cyclodextrin alone reduced lipid accumulation and lysosome size whereas treatment with other cyclodextrins alone did not have a profound effect. Moreover, the combination of δ-tocopherol and methyl-β-cyclodextrin resulted in a significant reduction in lipid accumulation and lysosome size.

Figure 7:
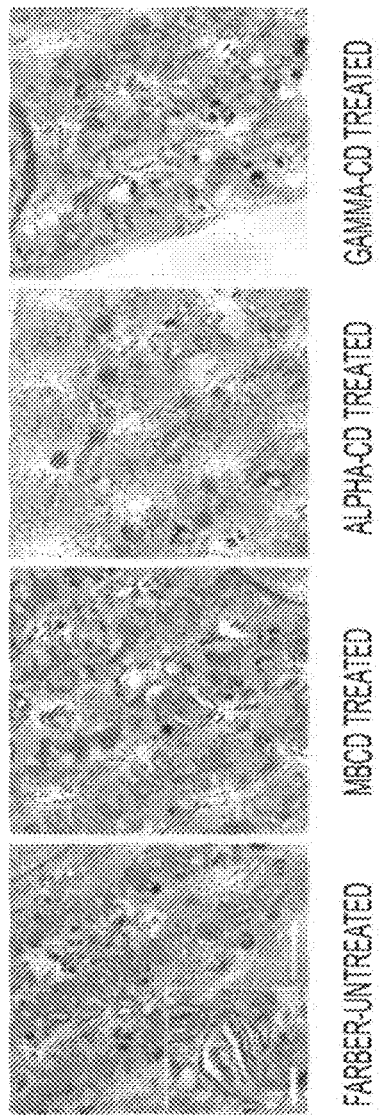
FIG. 7 is a set of photographs showing the electron microscopic analysis of Farber fibroblasts treated with methyl-β cyclodextrin (MBCD), α-cyclodextrin (alpha CD), or γ-cyclodextrin (gamma-CD).
Figure 8:
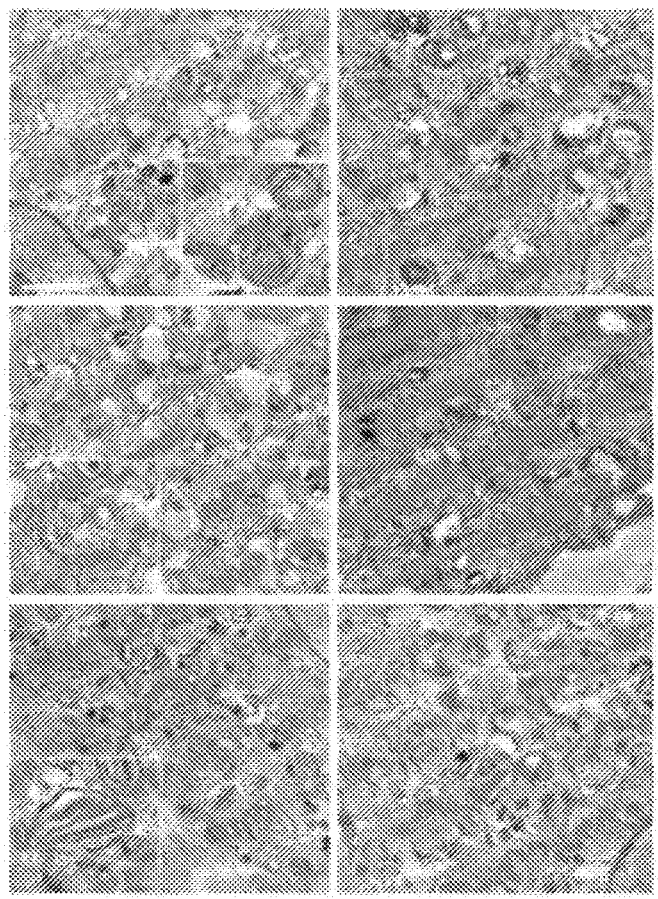
FIG. 8 is a set of photographs showing the electron microscopic analysis of Tay-Sach, Fabry, and Farber fibroblasts treated with methyl-β cyclodextrin (MBCD).
Figure 9:
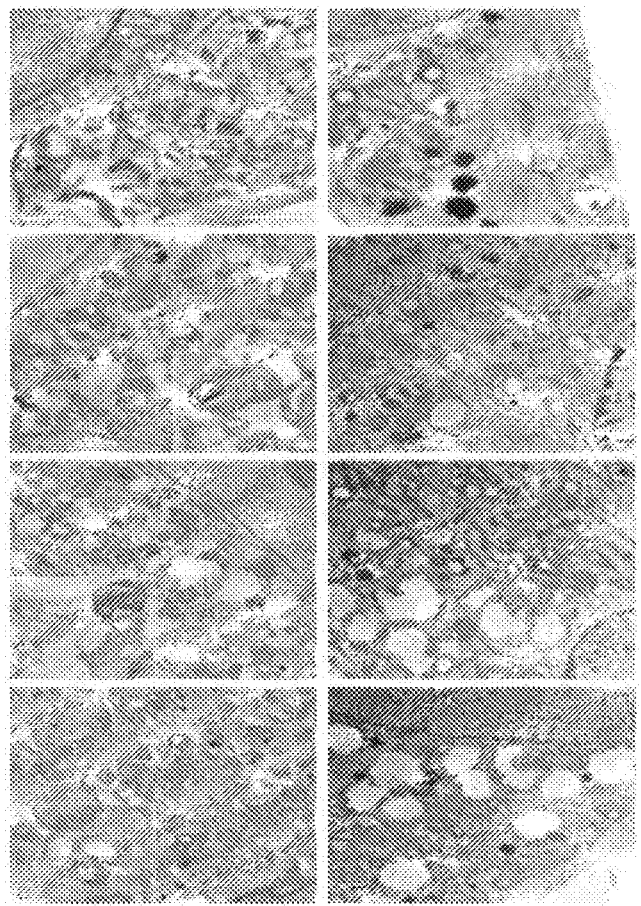
FIG. 9 is a set of photographs showing the electron microscopic analysis of Wolman, NPA, Batten, and MSIIIB fibroblasts treated with ethyl-β cyclodextrin (MBCD).
Figure 10:
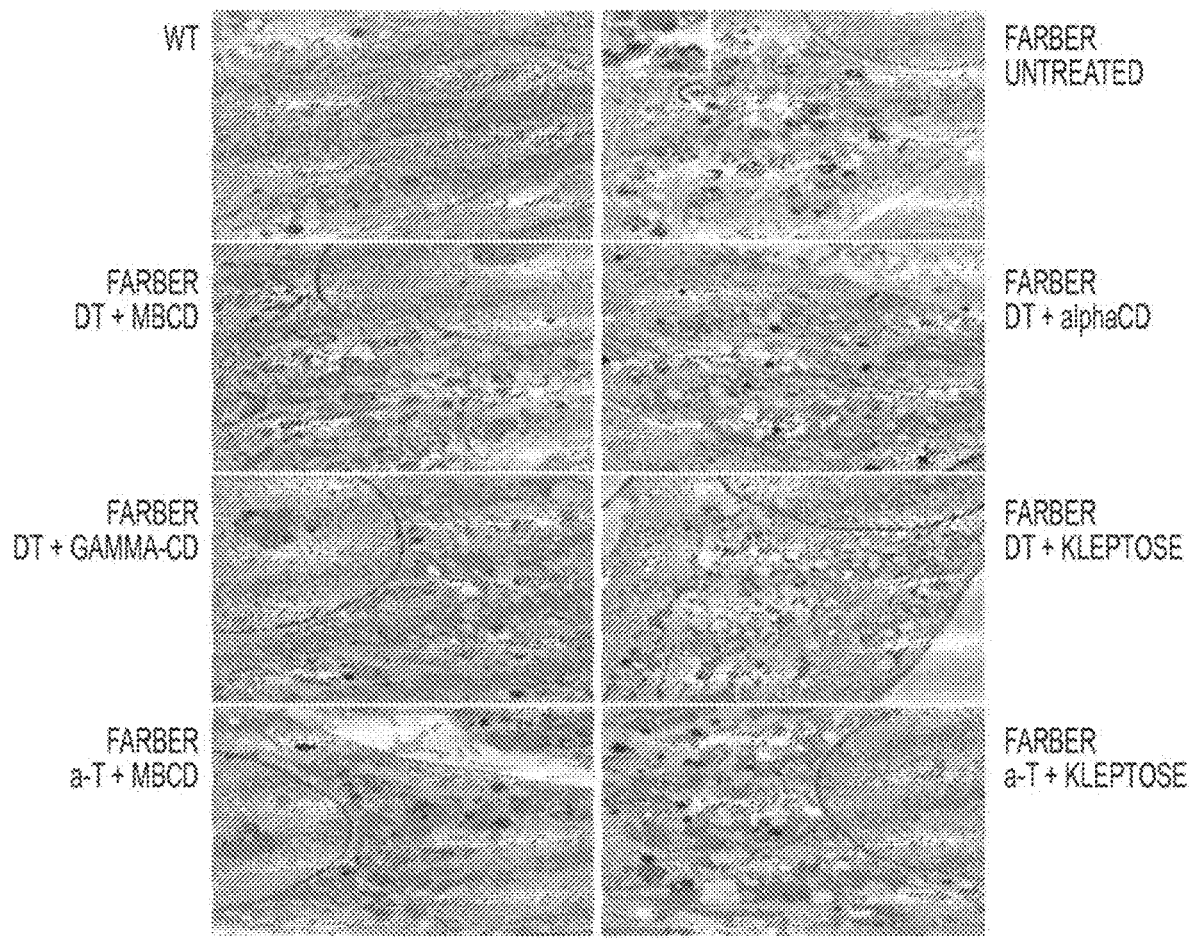
FIG. 10 is a set of photographs showing the electron microscopic analysis of Farber fibroblasts treated with δ-Tocopherol (DT) and methyl-β cyclodextrin (MBCD); δ-Tocopherol (DT) and α-cyclodextrin (a-T); δ-Tocopherol (DT) and γ-cyclodextrin (gamma-CD); δ-Tocopherol (DT) and Kleptose (also known as HBCD); α-Tocopherol (a-T) and methyl-β cyclodextrin (MBCD); and α-Tocopherol (a-T) and Kleptose. KLEPTOSE or TRAPPSOL are the brand names of the chemical HBCD or HBPCD.

Example 2: δ-Tocopherol and Cyclodextrin Treatment Resulted in Alleviation of the Pathological Ultrastructural Changes in Lysosomes of Cells with Lysosome Storage Disorders The effects of δ-tocopherol and methyl-β-cyclodextrin on the ultrastructural pathology of lysosomes in lysosome storage disorder cells were investigated by electron microscopy. In brief, following treatment of wild-type and lysosome storage disorder fibroblasts with δ-tocopherol, methyl-β-cyclodextrin, or δ-tocopherol and methyl-β-cyclodextrin, the fibroblasts were fixed and embedded. Thin sections of the embedded cells were then prepared and the ultrastructural pathology was examined by electron microscopy. As shown in FIG. 6, untreated Wolman fibroblasts have lamellated and osmophilic structures within the lysosomes. In addition, the cells also have the typical elongated and cleft-shaped lipid droplets in the lysomes. However, these abnormal structures were significantly reduced by treatment with δ-tocopherol and/or methyl-β-cyclodextrin. The effects of δ-tocopherol and/or methyl-β-cyclodextrin on the ultrastructural pathology of other lysosome disorder fibroblasts-Farber (FIGS. 7,8 and 10); Tay-Sachs (FIG. 8); Fabry (FIG. 8); Wolman (FIG. 9); NPA (FIG. 9); Batten (FIG. 9); MSIIB (FIG. 9)—were analyzed by electron microscopy. As shown in FIGS. 7-10, treated cells appear as typical fibroblasts (elongated shape, well developed nuclei, normal mitochondria, swollen smooth and rough ER) but with significant amounts of endosomal (in particular multivesicular bodies) and lysosomal compartments filled with lipid droplets and multilamellar bodies. These compartments are typical for Farber cells as seen before. Most cells have only small areas of these structures but a few cells are very much filled with these structures.

Example 3: Effect of Cyclodextrin in Single Use and in Combination with δ-Tocopherol in Human NPC1 Fibroblasts and Neural Stem Cells (NPC-NSCs)

Figure 11A:
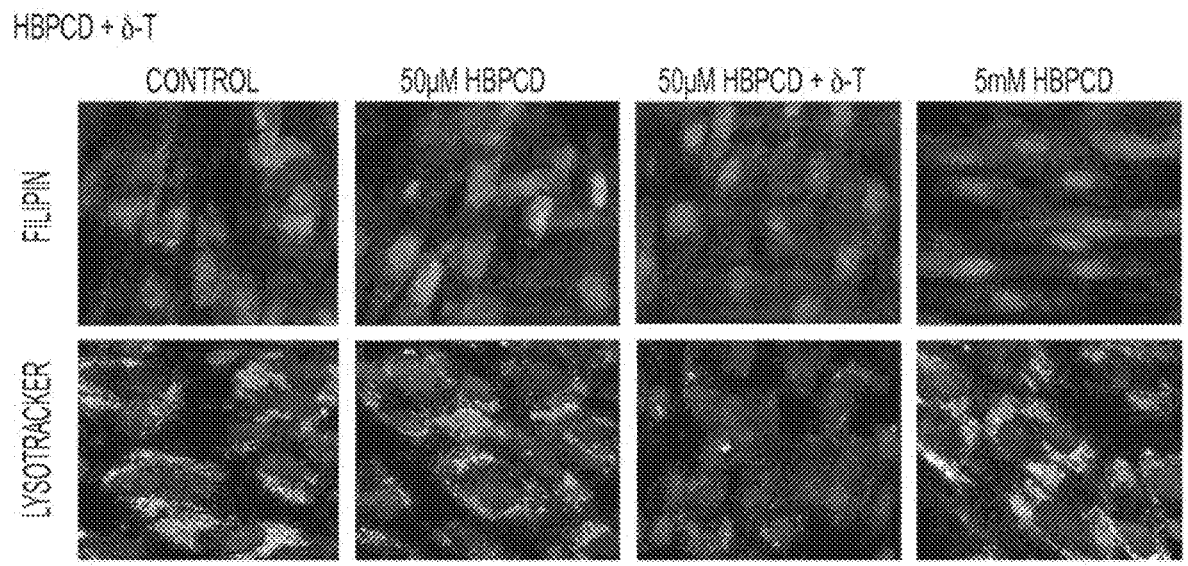
FIG. 11 (A and B) is a set of photographs that shows the effects of cyclodextrins and delta-tocopherol on reduction of cholesterol accumulation (Amplex-re-cholesterol assay and filipin staining) and enlarged lysosomes (Lysotracker staining) in the NPC1 skin fibroblasts. Methyl-β cyclodextrin (MBCD), HBPCD (Kleptose).
Figure 11B:
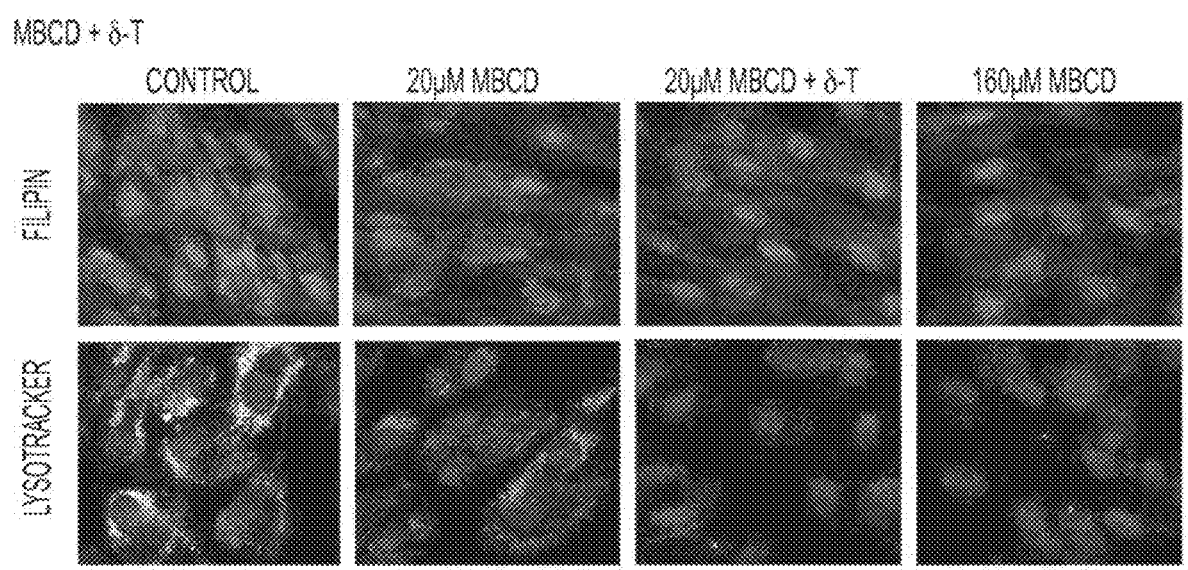

In another set of experiments, in skin fibroblasts derived from NPC1 patients, high concentrations of HBPCD (in millimolars) is needed for reduction of cholesterol accumulation and enlarged lysosomes (FIG. 11A). However, the small concentration of 50 μM of HBPCD in combination with 10 μM delta-tocopherol reached the same effect as 5 mM HBPCD. Although 160 μM MBCD almost completely reversed the phenotype of NPC1 cells, a much smaller concentration of 20 μMBCD in combination with 10 μM delta-tocopherol reached the similar results as those obtained with higher concentration of MBCD used along (FIG. 11B). Together, the data indicate that MBCD is more potent (over 30 fold) than HBPCD for reduction of cholesterol accumulation and enlarged lysosome size in NPC1 fibroblasts. In the combination with 10 μM delta-tocopherol, much smaller concentrations of HBPCD and MBCD are needed compared to those when both drugs used along.

Figure 12A:
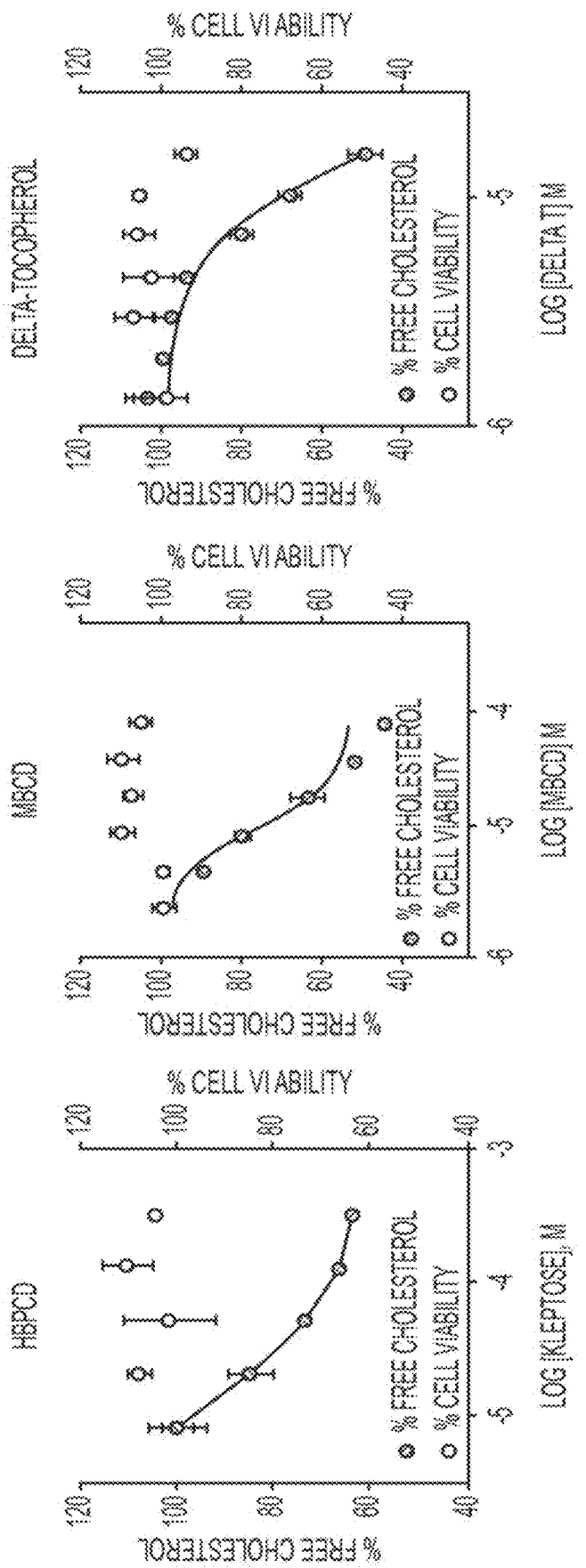
FIGS. 12(A and B) shows the effects of cyclodextrins and delta-tocopherol on reduction of cholesterol accumulation (Amplex-red cholesterol assay and filipin staining) and enlarged lysosomes (Lysotracker staining) in the NPC1 neuronal cells (NPC1-NSCs). (A) shows concentration responses determined in Amplex-red cholesterol assay. (B) shows filipin and lysotracker staining. Methyl-β cyclodextrin (MBCD), δ-Tocopherol (δ-T)
Figure 12B:
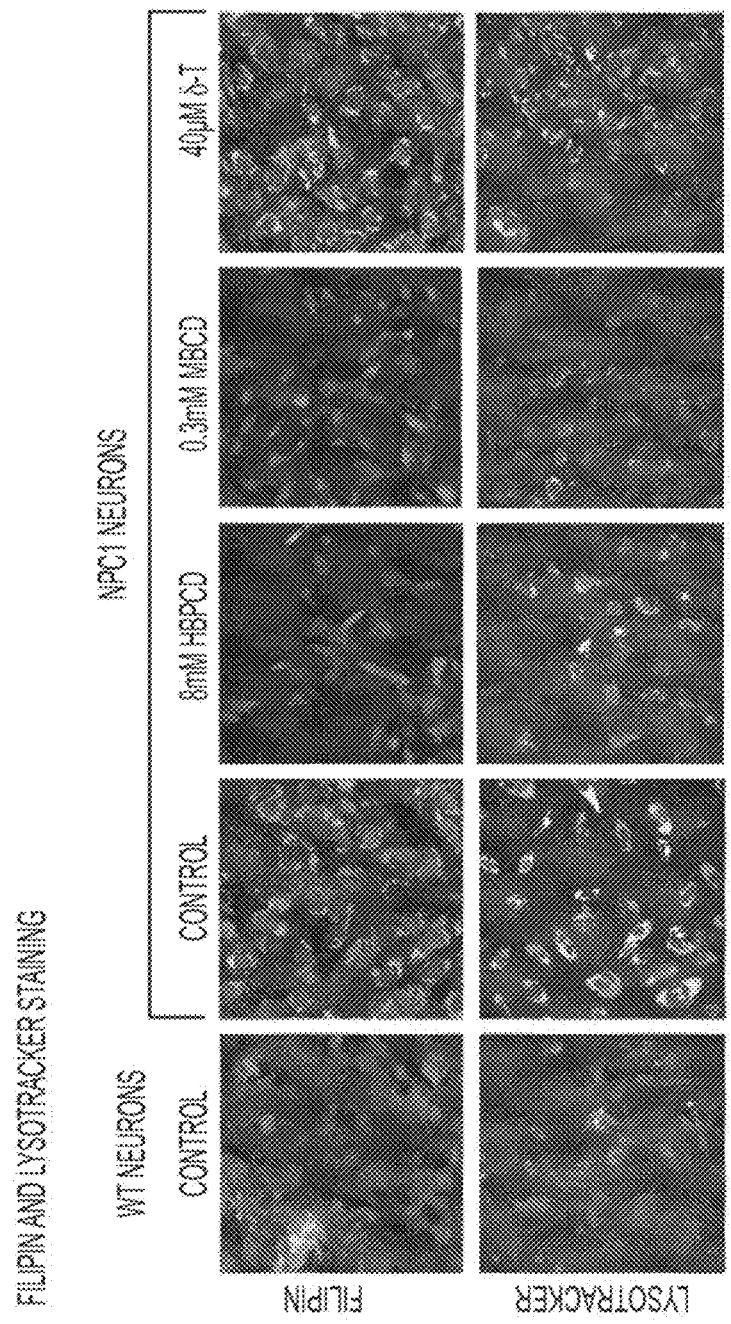

Example 4: Effect of Cyclodextrin in Single Use and in Combination with δ-Tocopherol in Neural Cells Derived from NPC1 Patients Since major symptoms of NPC disease are within the central nervous system, the human NPC1 neuronal cells are better representative as a NPC disease model for drug evaluation. Induced pluripotent stem cells (IPSCs) from the NPC1 skin fibroblasts were generated and differentiated into neural stem cells (NPC1-NSCs). In the Amplex-red cholesterol assay, the IC50 values of HBPCD and MBCD were 12 and 10 μM, respectively in the NPC1-NSCs, while the IC50 for delta-tocopherol was 18 μM (FIG. 12A). In the fluorescence microscopy experiments, the effects of HBPCD and MBCD on reduction of cholesterol accumulation (filipin staining) and enlarged lysosomes (Lysotracker staining) were also better than those of delta-tocopherol (FIG. 12B). Taken together, the data indicate that HBPCD is much more potent in the human NPC1 neuronal cells than that in the NPC1 skin fibroblasts, whereas the potency of delta-tocopherol is weaker in NPC1 neuronal cells compared to that in the NPC1 fibroblasts.

Figure 13A:
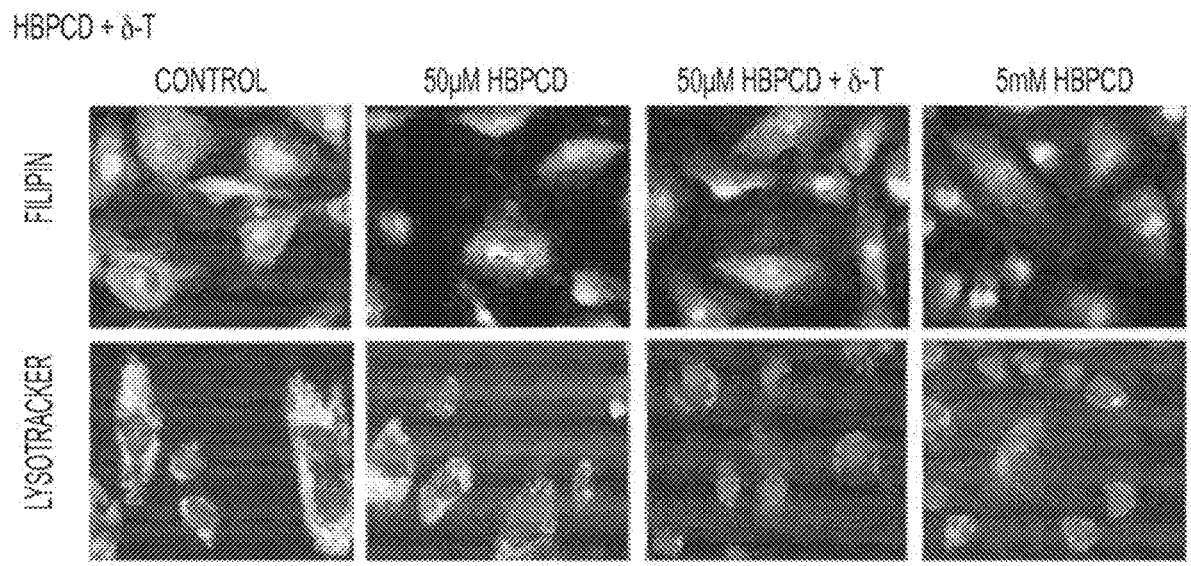
FIG. 13 (A and B) is a set of photographs that shows a comparison of the effect of single use of cyclodextrins with that in a combination with delta-tocopherol on reduction of cholesterol accumulation (filipin staining) and enlarged lysosomes ((Lysotracker staining) in NPC1 neuronal cells (NPC1-NSCs). (A) HBPCD+δ-Tocopherol. (B) MBCD+δ-Tocopherol.
Figure 13B:
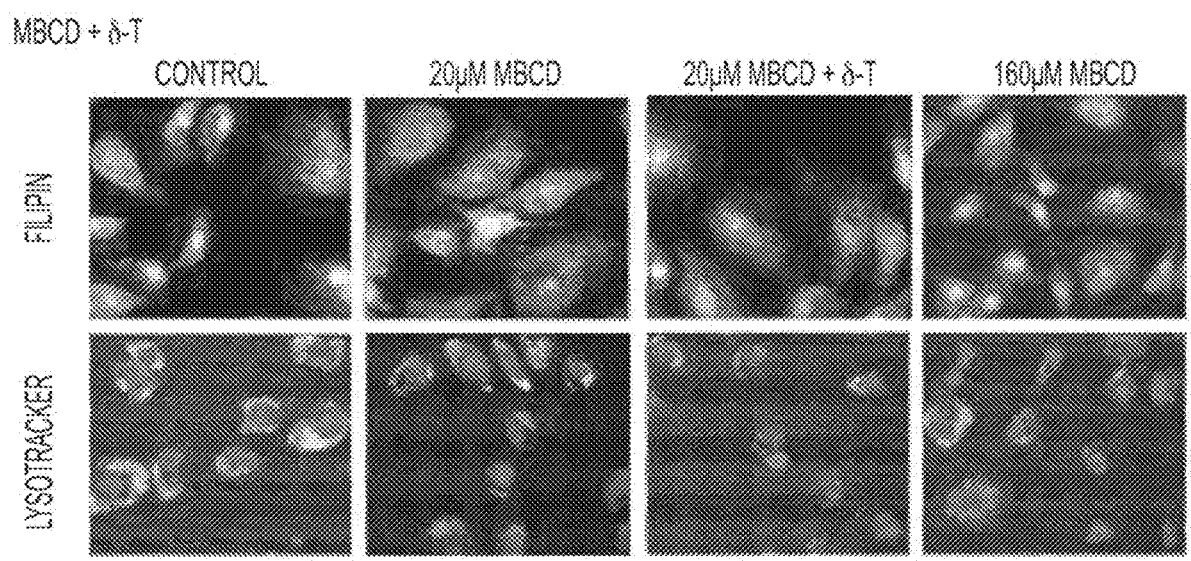

Example 5: Combination Therapy of Cyclodextrin and δ-Tocopherol Effectively Reduced the Concentrations of Individual Compounds and Increased the Effect on Reduction of Cholesterol Accumulation and Enlarged Lysosomes in NPC1-NSCs A much reduced concentration of 50 μM HBPCD in combination with 10 μM delta-tocopherol was determined to reach the same effect of 5 mM HBPCD used alone on reduction of cholesterol accumulation and enlarged lysosomes in the NPC1-NSCs (FIG. 13A). Similarly, the effect of 20 μM MBCD in combination with 10 μM delta-tocopherol was similar as 160 μM MBCD used alone in the NPC1-NSCs (FIG. 13B). The data demonstrate that the combination therapy of lower concentration of cyclodextrin and delta-tocopherol could achieve the similar therapeutic effect on reduction of cholesterol accumulation and enlarged lysosomes in the NPC1 neuronal cells as the large concentrations of both compounds when they use along. This concentration reduction of HBPCD or MBCD needed for the treatment of NPC1 in combination with low concentration of delta-tocopherol may be important for the clinical use in patients.

Dosage recommendations taken from the studies using human NPC1 neutral stem cells (NPSCs) are as follows: (1) The IC50 value for HBPCD on reduction of cholesterol accumulation measured by the Amplex-red cholesterol assay is 50 μM and IC50 for delta-tocopherol is 15 μM. Thus, the ratio is 3.3 fold. (2) In combination therapy experiment, 50 μM HBPCD+10 μM delta-tocopherol significant reduced cholesterol accumulation that is comparable with 5 mM HBPCD, while 50 μM HBPCD or 10 μM delta-tocopherol along did not show the significant cholesterol reduction effect. (3) The molecule weight ratio of HBPCD (MW=1380.25) and delta-tocopherol (MW=402.65) is 3.4 fold.

Given a mouse body weight of 25 g, where brain:body ratio is 1:40, an assuming a complete distribution of HBPCD and delta-tocopherol after direct central envious system injection of compound by intracerebroventricular injection or intrathecal injection, a preferred single use of cyclodextrin for mammals including humans is from 0.1 mg/Kg to 8 mg/Kg, more preferably 0.5 mg/kG or 1.0 mg/Kg to 2 mg/Kg, 3 mg/Kg, 4 mg/Kg, 5 mg/Kg, 6 mg/Kg, 7 mg/Kg or 84 mg/Kg. One specific preferred single use of cyclodextrin for mammals including humans is 3 mg/Kg. In a combination therapy of a cyclodextrin compound administered together or otherwise in conjunction with a vitamin E compound such as delta-tocopherol, a preferred single dose for a mammal including a human may be from 0.05 to 1 mg/kg for each of the cyclodextrin compound and vitamin E compound (such as delta-tocopherol), more preferably 0.1 mg/Kg to 0.5 mg/Kg, 0.6 mg/Kg or 0.7 mg/Kg for each of a cyclodextrin compound and vitamin E compound such as delta-tocopherol still more preferably 0.1 mg/Kg to 0.3 mg/Kg or 0.4 mg/Kg for each of a cyclodextrin compound and vitamin E compound such as delta-tocopherol.

Figure 14:
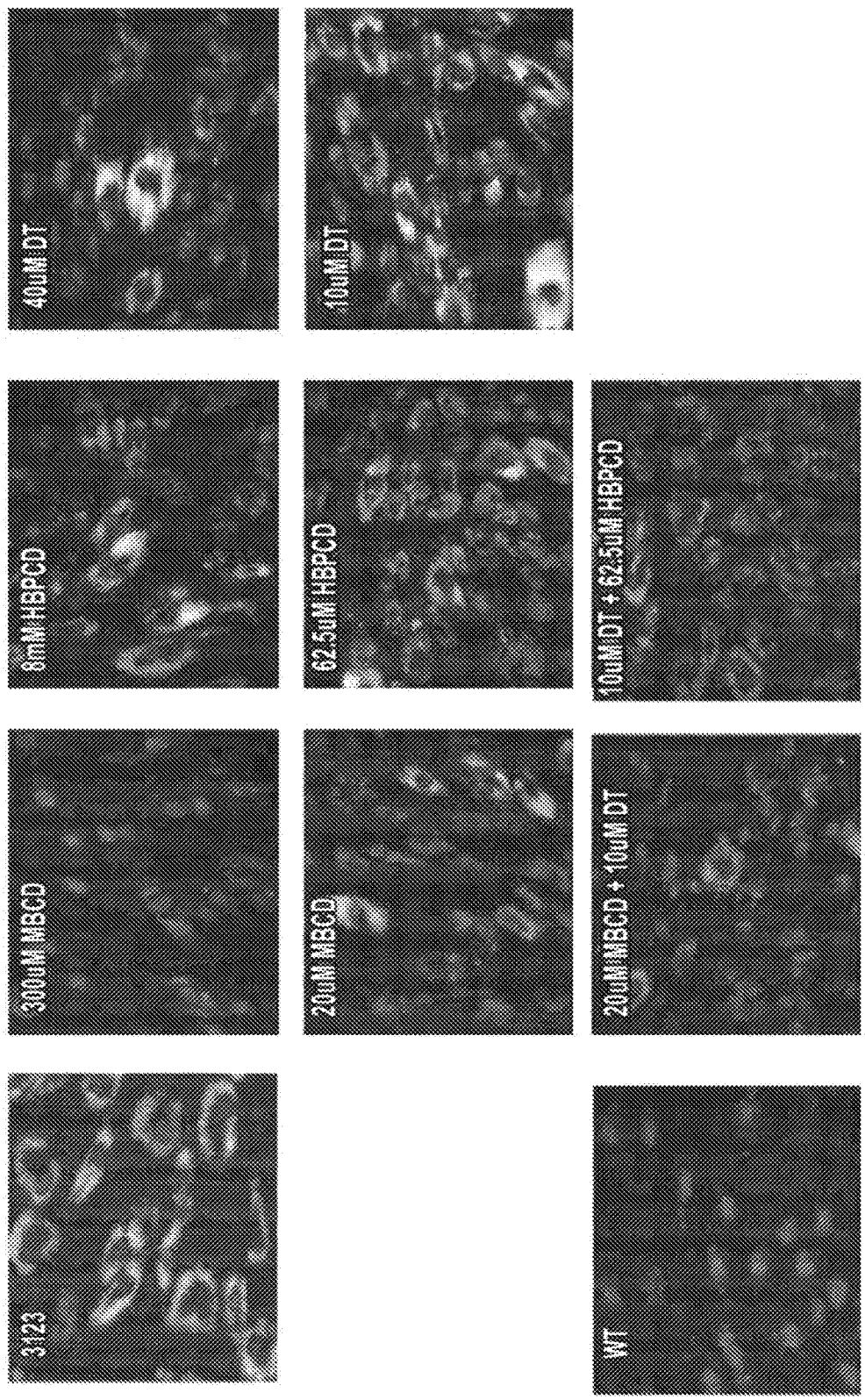
FIG. 14 is a set of photographs showing lysotracker staining in 3123 treated with methyl-β cyclodextrin (MBCD); HBPCD or δ-Tocopherol (DT).
Figure 15:
FIG. 15 is a set of photographs showing lysotracker staining in ML111 treated with methyl-β cyclodextrin (MBCD); HBPCD or δ-Tocopherol (DT).
Figure 16:
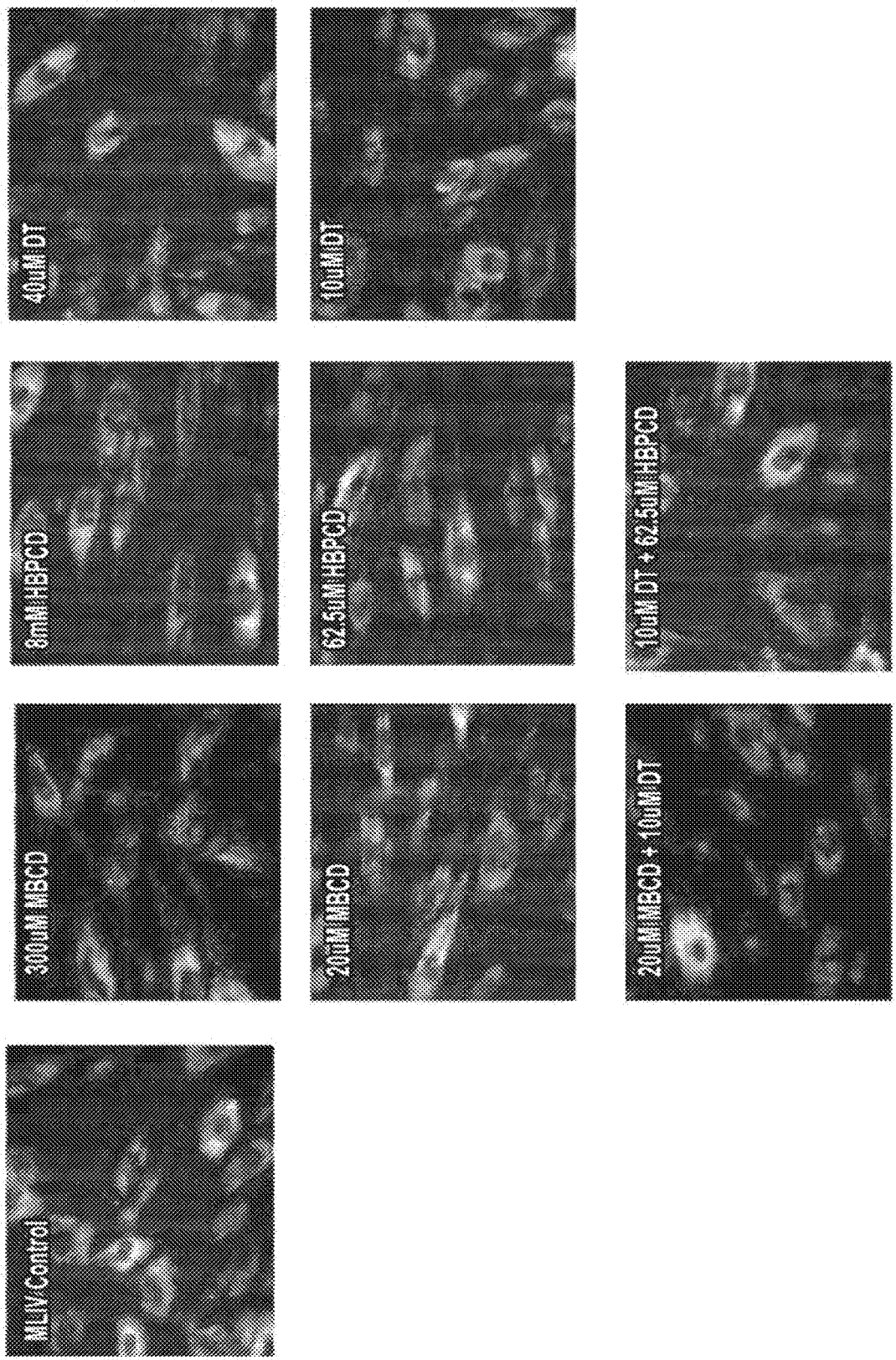
FIG. 16 is a set of photographs showing lysotracker staining in MLIV treated with methyl-β cyclodextrin (MBCD); HBPCD or δ-Tocopherol (DT).
Figure 17:
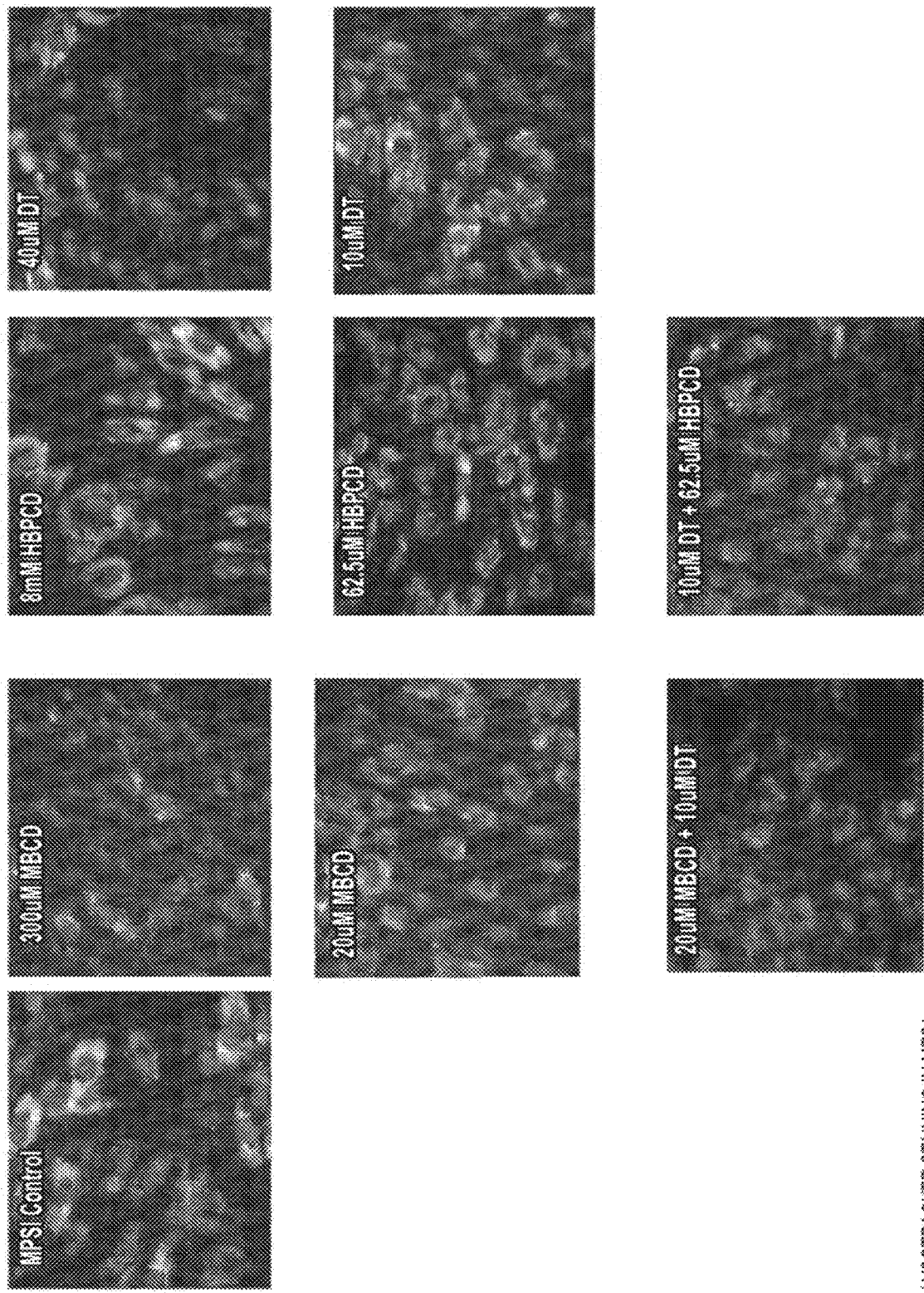
FIG. 17 is a set of photographs showing lysotracker staining in MPSI treated with methyl-β cyclodextrin (MBCD); HBPCD or δ-Tocopherol (DT).
Figure 18:
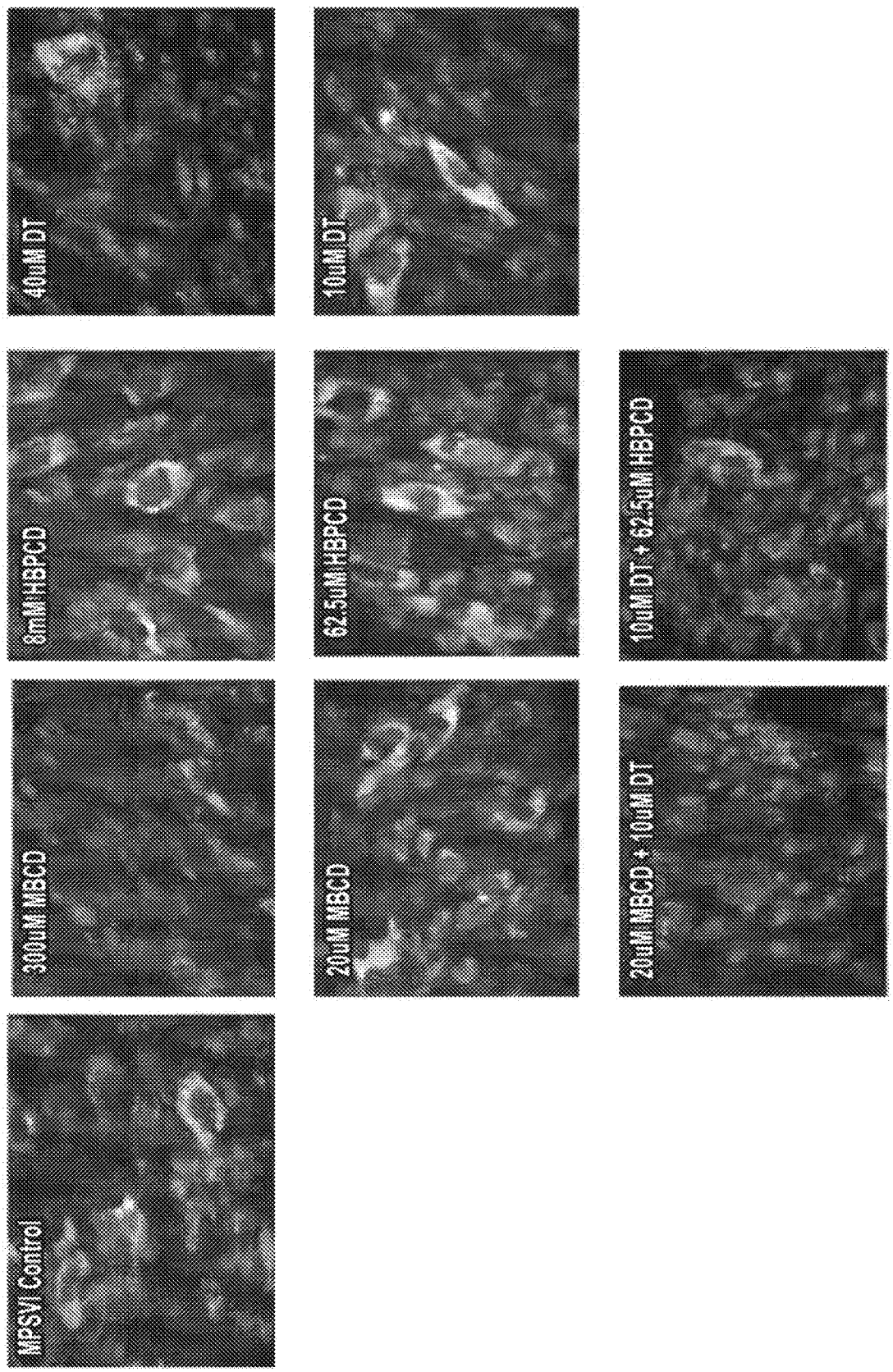
FIG. 18 is a set of photographs showing lysotracker staining in MPSVI treated with methyl-β cyclodextrin (MBCD); HBPCD or δ-Tocopherol (DT).

Example 6: Effects of Cyclodextrin Single Use and Combination Therapy of Cyclodextrin with δ-Tocopherol The effects of cyclodextrin in single use and in combination therapy with delta-tocopherol have been determined in patient derived skin fibroblasts with nine types of lysosomal storage diseases including NPC1 (FIG. 14), Batten, Farber, ML III (FIG. 15), MLIV (FIG. 16), MPS1 (FIG. 17), MPS VI (FIG. 18), NPA and Wolman disease. It was found that for single compound use, 8 mM HBPCD or 300 μM MBCD were needed for the significant effect on reduction of the enlarged lysosome size in those cells. However, in a combination with 10 μM delta-tocopherol, 500 μM HBPCD or 20 μM MBCD significantly reduced enlarged lysosomes in these cells. the results indicate an additive/synergistic effect of cyclodextrin with delta-tocopherol on reduction of enlarged lysosomes in the primary fibroblasts derived from patients with those nine lysosomal storage diseases. The results also indicate that the dose of cyclodextrin can be reduced 10 fold or more when it is used in combination with delta-tocopherol. The significant reduction of cyclodextrin dose in combination with delta-tocopherol is important for the treatment of lysosomal storage diseases because the high dose of cyclodextrin may cause server side effects in prolonged treatment process (it is possible that many of these patients may need a life time treatment).

In addition, the high plasma and brain concentrations of cyclodextrin are difficult to achieve in the treatment of LSD patients. The 10 fold reductions of cyclodextrin concentration required in the combination therapy with delta-tocopherol makes the clinical use of cyclodextrin in LSD patients more feasible. Furthermore, delta-tocopherol is difficult to be dissolved in aqueous solution for use in patients that can be resolved in the combination therapy because cyclodextrin can facilitate delta-tocopherol dissolving in solution.

Below is Table 1, showing the cell lines used for the above referenced studies.

TABLE 1

| Eponym of disease | Disease name | Abbreviation | Affected gene | Protein | Accumulated Lipid | Genotype | Coriell Catalog # |
|---|---|---|---|---|---|---|---|
| Batten | Ceroid lipofuscinosis, neuronal 2 | CLN2 | TPP1 | Tripeptidyl peptidase I | lipopigments (lipofuscin) | p.R127X, p.R208X | GM16485 |
| Fabry | Alpha-galactosidase A deficiency | | GLA | Alpha galactosidase A | globotriaosylceramide | p.W162X, rs2071397 rs2071228 | GM00107 |
| Farber | Lipogranulomatosis | | AC | Acid ceramidase (N-acylsphingosine amidohydrolase) | ceramide | p.Y36C, p.Y36C | GM20015 |
| Nieman n-Pick, type C1 | | NPC1 | NPC1 | NPC1 | Unesterified cholesterol | p.P237S, p.I1061T | GM03123 |
| Nieman n-Pick, type C2 | | NPC2 | NPC2 | NPC2 | Unesterified cholesterol | p.C93F, p.C93F | GM17910 |
| Nieman n-Pick, type A | | NPA | ASM | Acid sphingomyelinase | Sphingomyelin | p.L302P, p.L302P | GM16195 |
| Sanfilippo type B | Mucopolysaccharidosis III type B | MPS IIIB | NAGLU | N-acetyl-alpha-D-glucosaminidase | Partially degraded heparan sulfate | p.R297X, p.R643H | GM02552 |
| Tay-Sachs | GM2 gangliosidosis | TSD | | Beta hexosaminidase A | GM2 ganglioside | c.1278ins TATC c.1278ins TATC | GM00221 |
| Wolman | Lysosomal acid lipase deficiency | | LAL | Lysosomal acid lipase | Cholesteryl ester & triglycerides | unknown | GM11851 |

The contents of all references (including literature references, issued patents, published patent applications, and co-pending patient applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

What is claimed is:

1. A method of treating Battens disease, Farber disease, mucolipidosis type III (MLIII), mucolipidosis type IV (MLIV), mucopolysaccharidosis type I (MPSI), or mucopolysaccharidosis type VI (MPSVI) in a human, comprising administering to the human in need thereof an effective amount of a hydroxypropyl-β-cyclodextrin compound, or a pharmaceutically acceptable salt, solvate or hydrate thereof, wherein the hydroxypropyl-β-cyclodextrin compound is administered intracranially.

2. The method of claim 1, wherein the hydroxypropyl-β-cyclodextrin compound comprises from one to ten hydroxypropyl groups.

3. The method of claim 1, wherein the hydroxypropyl-β-cyclodextrin compound is administered intrathecally, intraventricularly, intracerebrally, or epidurally.

4. The method of claim 3, wherein the hydroxypropyl-β-cyclodextrin compound is administered intrathecally.

5. The method of claim 1, wherein the hydroxypropyl-β-cyclodextrin compound is administered in combination with a pharmaceutically acceptable carrier or excipient.

6. The method of claim 1, wherein the hydroxypropyl-β-cyclodextrin compound comprises an average of four hydroxypropyl groups.

* * * * *